US012734362B2

(12) United States Patent
Esteller et al.

(10) Patent No.: US 12,734,362 B2
(45) Date of Patent: Sep. 15, 2026

(54) METHOD AND APPARATUS FOR DETERMINING TRUE NEURAL ACTIVATION CHANGES

(71) Applicant: Boston Scientific Neuromodulation Corporation, Valencia, CA (US)

(72) Inventors: Rosana Esteller, Santa Clarita, CA (US); Max Witwer, Grand Junction, CO (US); Tianhe Zhang, Studio City, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 283 days.

(21) Appl. No.: 18/380,106

(22) Filed: Oct. 13, 2023

(65) Prior Publication Data

US 2024/0123234 A1 Apr. 18, 2024

Related U.S. Application Data

(60) Provisional application No. 63/416,123, filed on Oct. 14, 2022.

(51) Int. Cl.
*A61N 1/36* (2006.01)
*G06F 18/213* (2023.01)

(52) U.S. Cl.
CPC ..... *A61N 1/36139* (2013.01); *A61N 1/36178* (2013.01); *G06F 18/213* (2023.01); *G06F 2218/10* (2023.01)

(58) Field of Classification Search
CPC ........................ A61N 1/36139; A61N 1/36178
(Continued)

(56) References Cited

U.S. PATENT DOCUMENTS

| | | | |
|---|---|---|---|
| 11,583,678 | B2 | 2/2023 | Esteller et al. |
| 2014/0012157 | A1 | 1/2014 | Gilhuly |

(Continued)

FOREIGN PATENT DOCUMENTS

| | | | |
|---|---|---|---|
| WO | WO-2020206152 | A1 | 10/2020 |
| WO | WO-2022031645 | A1 | 2/2022 |
| WO | WO-2022072256 | A1 | 4/2022 |
| WO | WO-2022183161 | A1 | 9/2022 |
| WO | WO-2024081389 | A1 | 4/2024 |
| WO | WO-2025090310 | A1 | 5/2025 |

OTHER PUBLICATIONS

"International Application Serial No. PCT/US2023/035076, International Preliminary Report on Patentability mailed Apr. 24, 2025", 8 pgs.

(Continued)

*Primary Examiner* — Nicole F Johnson
(74) *Attorney, Agent, or Firm* — Schwegman Lundberg & Woessner, P.A.

(57) ABSTRACT

An examples of a system for delivering neurostimulation to a patient may include a stimulation output circuit configured to deliver the neurostimulation, a sensing circuit configured to sense a neural signal indicative of neural responses to the neurostimulation, and stimulation control circuit. The stimulation control circuit may be configured to control the delivery of the neurostimulation using a plurality of stimulation parameters and may be configured to detect morphological features of the neural responses, to produce a neural response parameter using the detected morphological features, to detect a change in the sensed neural signal, to analyze the produced neural response parameter for attributing the detected change to one of a neural activation change in the patient or a body movement of the patient, and to control a dynamically controlled stimulation parameter of the plurality of stimulation parameters using the sensed neural signal and an outcome of the analysis.

20 Claims, 22 Drawing Sheets

(58) Field of Classification Search
USPC .............................................................. 607/62
See application file for complete search history.

(56) References Cited

U.S. PATENT DOCUMENTS

| | | | |
|---|---|---|---|
| 2015/0360031 | A1 | 12/2015 | Bornzin et al. |
| 2017/0128725 | A1 | 5/2017 | Kim et al. |
| 2020/0316382 | A1* | 10/2020 | Esteller ................ A61N 1/0551 |
| 2021/0138245 | A1 | 5/2021 | Carroll |
| 2022/0266022 | A1 | 8/2022 | Steinke et al. |
| 2022/0266027 | A1* | 8/2022 | Zhang ................ A61N 1/36178 |
| 2022/0331589 | A1 | 10/2022 | Bittner et al. |
| 2025/0128070 | A1 | 4/2025 | Moffitt |

OTHER PUBLICATIONS

"International Application Serial No. PCT/US2023/035076, International Search Report mailed Feb. 5, 2024", 4 pgs.
"International Application Serial No. PCT/US2023/035076, Written Opinion mailed Feb. 5, 2024", 6 pgs.
"International Application Serial No. PCT/US2024/051254, International Search Report mailed Jan. 27, 2025", 4 pgs.
"International Application Serial No. PCT/US2024/051254, Written Opinion mailed Jan. 27, 2025", 6 pgs.
Stanslaski, Scott, et al., "A Chronically Implantable Neural Coprocessor for Investigating the Treatment of Neurological Disorders", IEEE Transactions on Biomedical Circuits and Systems, US, vol. 12, No. 6, (Dec. 1, 2018), 1230-1245.

* cited by examiner

STIMULATION
DORSAL
SENSING
EPIDURAL SPACE
DURA
CSF
SPINAL CORD
VENTRAL

STIMULATION
DORSAL
SENSING
EPIDURAL SPACE
DURA
CSF
SPINAL CORD
VENTRAL

STIMULATION
DORSAL
SENSING
EPIDURAL SPACE
DURA
CSF
SPINAL CORD
VENTRAL

METHOD AND APPARATUS FOR DETERMINING TRUE NEURAL ACTIVATION CHANGES

CLAIM OF PRIORITY

This application claims the benefit of U.S. Provisional Application No. 63/416,123, filed on Oct. 14, 2022, which is hereby incorporated by reference in its entirety.

TECHNICAL FIELD

This document relates generally to neurostimulation and more particularly to a neurostimulation system that determines true neural activation changes for use in control of stimulation delivery.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered to a patient in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. The stimulation parameters may be set and/or adjusted based on signals sensed from the patient and indicative of the patient's conditions and/or the patient's response to the delivery of the neurostimulation. For example, a closed-loop control system may sense the patient's neural responses to the delivery of the neurostimulation and adjust one or more stimulation parameters in response to a change in the sensed neural responses.

SUMMARY

An Example (e.g., "Example 1") of a system for delivering neurostimulation to a patient is provided. The system may include a stimulation output circuit, a sensing circuit, and a stimulation control circuit. The stimulation output circuit may be configured to deliver the neurostimulation. The sensing circuit may be configured to sense a neural signal indicative of neural responses. The neural responses are each a response to the delivery of the neurostimulation. The stimulation control circuit may be coupled to the stimulation output circuit and the sensing circuit and may be configured to control the delivery of the neurostimulation using a plurality of stimulation parameters. The stimulation control circuit may include a measurement module, an input analyzer, and a feedback controller. The measurement module may be configured to detect morphological features of the neural responses and to produce a neural response parameter using the detected morphological features. The input analyzer may be configured to detect a change in the sensed neural signal and to analyze the produced neural response parameter for attributing the detected change to one of a neural activation change in the patient or a body movement of the patient. The feedback controller may be configured to control a dynamically controlled stimulation parameter of the plurality of stimulation parameters using the sensed neural signal and an outcome of the analysis.

In Example 2, the subject matter of Example 1 may optionally be configured such that the stimulation output circuit is configured to deliver neurostimulation pulses, the sensing circuit is configured to sense a neural signal indicative of evoked compound action potentials (ECAPs) each evoked by a pulse of the neurostimulation pulses, and the measurement module is configured to detect ECAP features each being a morphological feature of the ECAPs and to produce the neural response parameter using the detected ECAP features.

In Example 3, the subject matter of Example 2 may optionally be configured such that the measurement module is configured to measure the neural response parameter using the detected ECAP features.

In Example 4, the subject matter of any one or any combination of Examples 2 and 3 may optionally be configured such that the measurement module is configured to measure two or more parameters using the detected ECAP features and calculating the neural response parameter as a function of the measured two or more parameters.

In Example 5, the subject matter of any one or any combination of Examples 3 and 4 may optionally be configured such that the measurement module is configured to measure a time interval associated with at least one of the detected ECAP features.

In Example 6, the subject matter of any one or any combination of Examples 3 to 5 may optionally be configured such that the measurement module is configured to measure an amplitude parameter of the neural response parameters. The amplitude parameter is an amplitude associated with at least one of the detected ECAP features.

In Example 7, the subject matter of any one or any combination of Examples 3 to 6 may optionally be configured such that the measurement module is configured to measure at least one of a curve length or an area-under-the-curve of the neural response parameters. The curve length is a length of the sensed neural signal associated with at least one of the detected ECAP features. The area-under-the-curve is an area under the sensed neural signal associated with at least one of the detected ECAP features.

In Example 8, the subject matter of any one or any combination of Examples 3 and 4 may optionally be configured such that the measurement module is configured to detect at least one of a first negative peak (N1) or a second positive peak (P2) of the ECAP features and to measure at least one of:

- an N1-P2 Latency being a time interval between N1 and P2;
- an N1 latency being a time interval between delivery of a pulse of the neurostimulation pulses and N1;
- a P2 latency a time interval between delivery of a pulse of the neurostimulation pulses and P;
- an N1-P2 Range being a difference between amplitudes of N1 and P2;
- a dynamic curve length (CL) being a curve length measured from the sensed neural signal between N1 and P2; or a dynamic area under the curve (AUC) being an area under the sensed neural signal measured between N1 and P2.

In Example 9, the subject matter of any one or any combination of Examples 2 to 4 may optionally be configured such that the input analyzer is configured to determine whether the detected change indicates a neural activation change has occurred, and the feedback controller is configured to adjust the dynamically controlled stimulation parameter in response to a determination that the neural activation change has occurred and to keep the dynamically controlled stimulation parameter unchanged in response to a determination that the neural activation change has not occurred.

In Example 10, the subject matter of Example 9 may optionally be configured such that the input analyzer is configured to: determine a maximum variation of the neural response parameter for a segment of the neural signal sensed during body movements of the patient; and compare the maximum variation of the neural response parameter to a threshold variation, and the feedback controller is configured to: adjust the dynamically controlled stimulation parameter in response to the maximum variation of the neural response parameter exceeding the threshold variation; and keep the dynamically controlled stimulation parameter unchanged in response to the maximum variation of the neural response parameter not exceeding the threshold variation.

In Example 11, the subject matter of Example 9 may optionally be configured such that the input analyzer is configured to: determine a variation of the neural response parameter for a segment of the neural signal sensed during body movements of the patient; and compare the variation of the neural response parameter to each of a first variation template and a second variation template, and the feedback controller is configured to: adjust the dynamically controlled stimulation parameter in response to the variation of the neural response parameter being closer to the first variation template than to the second variation template; and keep the dynamically controlled stimulation parameter unchanged in response to the variation of the neural response parameter being closer to the second variation template than to the first variation template.

In Example 12, the subject matter of Example 9 may optionally be configured such that the neural response parameter is a latency parameter being a time interval associated with at least one of the detected ECAP features, and the input analyzer is configured to: deactivate the feedback controller in response to an adjustment count reaching a specified value N; determine a change of the latency parameter by a current value of the latency parameter to a previous value of the latency parameter; compare the change of the latency parameter change to a threshold change; activate the feedback controller in response to the change of the latency parameter change exceeding the threshold change; and keep the feedback controller inactivated in response to the change of the latency parameter change not exceeding the threshold change, and the feedback controller is configured to: adjust the dynamically controlled stimulation parameter when being activated; and increase the adjustment count by 1 in response to each adjustment.

In Example 13, the subject matter of any one or any combination of Examples 1 to 8 may optionally be configured such that the input analyzer is configured to determine a weighting factor as a function of the neural response parameter, and the feedback controller is configured to apply the weighting factor to the dynamically controlled stimulation parameter and to adjust the weighted dynamically controlled stimulation parameter.

In Example 14, the subject matter of Example 13 may optionally be configured such that the neural response parameter is a latency parameter being a time interval associated with at least one of the detected ECAP features.

An example (e.g., "Example 15") of a non-transitory computer-readable storage medium is also provided. The non-transitory computer-readable storage medium includes instructions, which when executed by a system, cause the system to perform a method for delivering neurostimulation to a patient. The method may include delivering the neurostimulation sensing a neural signal indicative of neural responses, and controlling the delivery of the neurostimulation using a plurality of stimulation parameters. The neural responses are each a response to the delivery of the neurostimulation. The controlling may include detecting morphological features of the neural responses, producing a neural response parameter using the detected morphological features, detecting a change in the sensed neural signal, analyzing the produced neural response parameter for attributing the detected change to one of a neural activation change in the patient or a body movement of the patient, and controlling a dynamically controlled stimulation parameter of the plurality of stimulation parameters using the sensed neural signal and an outcome of the analysis.

An example (e.g., "Example 16") of a method for delivering neurostimulation to a patient is also provided. The method may include delivering the neurostimulation from a stimulation output circuit, sensing a neural signal indicative of neural responses using a sensing circuit, and controlling the delivery of the neurostimulation using a processor using a plurality of stimulation parameters. The neural responses are each a response to the delivery of the neurostimulation. The controlling may include detecting morphological features of the neural responses, producing a neural response parameter using the detected morphological features, detecting a change in the sensed neural signal, analyzing the produced neural response parameter for attributing the detected change to one of a neural activation change in the patient or a body movement of the patient, and controlling a dynamically controlled stimulation parameter of the plurality of stimulation parameters using the sensed neural signal and an outcome of the analysis.

In Example 17, the subject matter of sensing the signal as found in Example 16 may optionally further include identifying a suitable type of parameter to be the neural response parameter using at least one of machine learning or artificial intelligence.

In Example 18, the subject matter of delivering the neurostimulation as found in any one or any combination of Examples 16 and 17 may optionally include delivering neurostimulation pulses, the subject matter of sensing the neural signal as found in any one or any combination of Examples 16 and 17 may optionally include sensing a neural signal indicative of evoked compound action potentials (ECAPs) each evoked by a pulse of the neurostimulation pulses, the subject matter of detecting the morphological features of the neural responses as found in any one or any combination of Examples 16 and 17 may optionally include detecting ECAP features each being a morphological feature of the ECAPs, and the subject matter of producing the neural response parameter as found in any one or any combination of Examples 16 and 17 may optionally include producing the neural response parameter using the detected ECAP features.

In Example 19, the subject matter of producing the neural response parameter as found in Example 18 may optionally include at least one of: measuring the neural response parameter using the detected ECAP features; or measuring two or more parameters using the detected ECAP features and calculating the neural response parameter as a function of the measured two or more parameters.

In Example 20, the subject matter of detecting the ECAP features as found in Example 19 may optionally include detecting at least one of a first negative peak (N1) or a second positive peak (P2), and the subject matter of producing the neural response parameter as found in Example 19 may optionally include measuring at least one of:

- an N1-P2 Latency being a time interval between N1 and P2;
- an N1 latency being a time interval between delivery of a pulse of the neurostimulation pulses and N1;
- a P2 latency a time interval between delivery of a pulse of the neurostimulation pulses and P;
- an N1-P2 Range being a difference between amplitudes of N1 and P2;
- a dynamic curve length (CL) being a curve length measured from the sensed neural signal between N1 and P2; or
- a dynamic area under the curve (AUC) being an area under the sensed neural signal measured between N1 and P2.

In Example 21, the subject matter of any one or any combination of Examples 16 to 19 may optionally further include determining whether the detected change indicates a neural activation change has occurred using the processor, and the subject matter of controlling the dynamically controlled stimulation parameter as found in any one or any combination of Examples 16 to 19 may optionally include adjusting the dynamically controlled stimulation parameter in response to a determination that the neural activation change has occurred and keeping the dynamically controlled stimulation parameter unchanged in response to a determination that the neural activation change has not occurred.

In Example 22, the subject matter of determining whether the detected change indicates a neural activation change has occurred as found in Example 21 may optionally include: determining a maximum variation of the neural response parameter for a segment of the neural signal sensed during body movements of the patient; and comparing the maximum variation of the neural response parameter to a threshold variation, and the subject matter of controlling the dynamically controlled stimulation parameter as found in Example 21 may optionally include: adjusting the dynamically controlled stimulation parameter in response to the maximum variation of the neural response parameter exceeding the threshold variation; and keeping the dynamically controlled stimulation parameter unchanged in response to the maximum variation of the neural response parameter not exceeding the threshold variation.

In Example 23, the subject matter of determining whether the detected change indicates a neural activation change has occurred as found in Example 21 may optionally include: determining a variation of the neural response parameter for a segment of the neural signal sensed during body movements of the patient; and comparing the variation of the neural response parameter to each of a first variation template and a second variation template, and the subject matter of controlling the dynamically controlled stimulation parameter as found in Example 21 may optionally include: adjusting the dynamically controlled stimulation parameter in response to the variation of the neural response parameter being closer to the first variation template than to the second variation template; and keeping the dynamically controlled stimulation parameter unchanged in response to the variation of the neural response parameter being closer to the second variation template than to the first variation template.

In Example 24, the neural response parameter as found in Example 21 is a latency parameter being a time interval associated with at least one of the detected ECAP features, the subject matter of determining whether the detected change indicates a neural activation change has occurred as found in Example 21 may optionally include: deactivating a closed-loop control in response to an adjustment count reaching a specified value N; determining a change of the latency parameter by a current value of the latency parameter to a previous value of the latency parameter; comparing the change of the latency parameter change to a threshold change; activating the closed-loop control in response to the change of the latency parameter change exceeding the threshold change; and keep the closed-loop control inactivated in response to the change of the latency parameter change not exceeding the threshold change, and the subject matter of controlling the dynamically controlled stimulation parameter as found in Example 21 may optionally include: adjusting the dynamically controlled stimulation parameter according to the closed-loop control when being activated; and increasing the adjustment count by 1 in response to each adjustment.

In Example 25, the subject matter of determining whether the detected change indicates a neural activation change has occurred as found in any one or any combination of Examples 16 to 19 may optionally include determining a weighting factor as a function of the neural response parameter, and the subject matter of controlling the dynamically controlled stimulation parameter as found in any one or any combination of Examples 16 to 19 may optionally include: applying the weighting factor to the dynamically controlled stimulation parameter; and adjusting the weighted dynamically controlled stimulation parameter.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
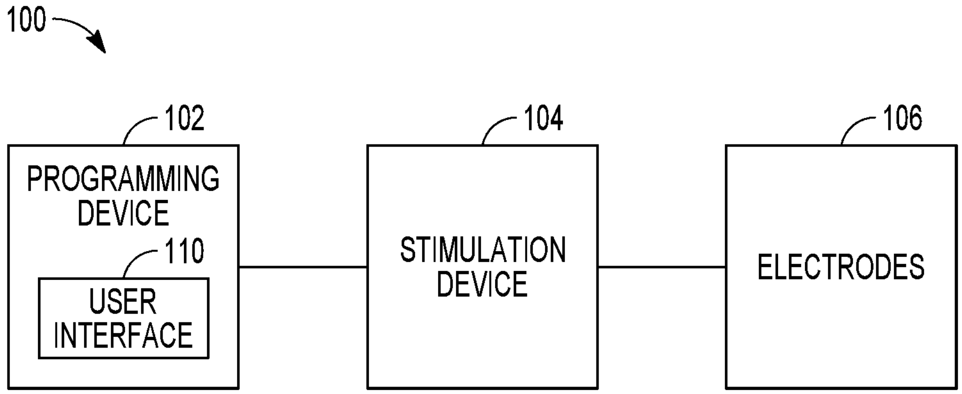
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can sense a neural signal from a patient, analyze the sensed signal to distinguish neural activation changes from other changes, and control delivery of neurostimulation to the patient using the sensed neural signal and an outcome of the analysis. In various embodiments, the neuromodulation system can include an implantable device configured to deliver neurostimulation (also referred to as neuromodulation) therapies, such as spinal cord stimulation (SCS), deep brain stimulation (DBS), peripheral nerve stimulation (PNS), and vagus nerve stimulation (VNS), and one or more external devices configured to program or adjust the implantable device for its operations and monitor the performance of the implantable device. In this document, unless noted otherwise, a "patient" includes a person receiving treatment delivered from, and/or monitored using, a neurostimulation system according to the present subject matter. A "user" includes a physician, other caregiver who examines and/or treats the patient using the neurostimulation system, or other person who participates in the examination and/or treatment of the patient using the neurostimulation system (e.g., a technically trained representative, a field clinical engineer, a clinical researcher, or a field specialist from the manufacturer of the neurostimulation system).

In SCS, one or more leads may be used to deliver neurostimulation and sense a neural signal with sensing and stimulation electrodes epidurally placed on the spinal cord of a patient. The stimulation and sensing locations can be separated by around 15 mm or more to reduce stimulus artifacts in sensing of neural responses such as the evoked compound action potentials (ECAPs). In various examples of an existing SCS system that controls delivery of neurostimulation using stimulation parameters that are adjusted according to an ECAP-based closed-loop control algorithm, it is assumed that the distance between the spinal cord and the stimulation electrode (herein referred to as "stimulation distance", or "$d_{stim}$") and the distance between the spinal cord and the sensing electrode (herein referred to as "sensing distance", or "$d_{sense}$") are equal (i.e., $d_{stim}=d_{sense}$). However, body movements of the patient causes the spinal cord to move within the cerebrospinal fluid (CSF) and causes shifts in the epidurally placed sensing and stimulation electrodes. Using a computational ECAP model of the spinal cord, responses of dorsal column fibers to various stimulation parameters and for various combinations of the stimulation distance and the sensing distance (including various instances for each of $d_{stim}=d_{sense}$, $d_{stim}>d_{sense}$, and $d_{stim}<d_{sense}$) were determined by simulations. The result demonstrated that the assumption of equal stimulation distance and sensing distance could lead to erroneous adjustments of stimulation parameters because an adjustment could be made in response to a change in the sensed neural signal that is caused by a body movement of the patient rather than a change in the patient's neural activation.

The present neurostimulation system distinguishes a detected change in the sensed neural signal caused by a movement of the patient (which should not cause adjustment of the stimulation parameters) from a detected change in the sensed neural signal caused by a neural activation change in the patient (which may correctly cause adjustment of the stimulation parameters) and adjusts one or more stimulation parameters accordingly. While sensing of a neural signal including ECAPs and adjustment of a stimulation current (also referred to as pulse amplitude) is specifically discussed as an example, the present subject matter can be applied to various other types of signals and stimulation parameters. Examples of the stimulation parameters include stimulation current (pulse amplitude), frequency (also referred to as rate), charge per second, charge per phase, pulse width, burst cycling times, and interphase interval (time between stimulation and recharging phases). In various embodiments, any one or any combination of such stimulation parameters can be adjusted for controlling neurostimulation according to the present subject matter.

FIG. 1 illustrates an embodiment of a neurostimulation system 100. System 100 includes electrodes (also referred to as contacts) 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for spinal cord stimulation (SCS) applications. Such SCS configuration includes various features that may simplify the task of the user in programming stimulation device 104 for delivering SCS to the patient, such as the features discussed in this document.

Figure 2:
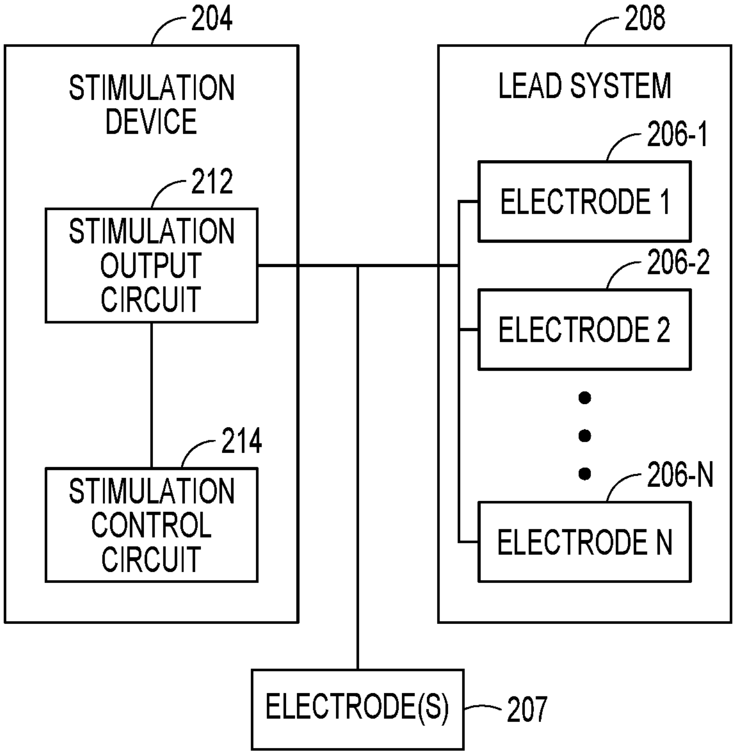
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 (also referred to as an electrode array in this document) distributed in the one or more leads. The plurality of electrodes 206 includes electrode 206-1, electrode 206-2, . . . electrode 206-N, each being a single electrically conductive contact providing for an electrical interface between stimulation output circuit 212 and tissue of the patient (and therefore also referred to as a contact in this document), where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
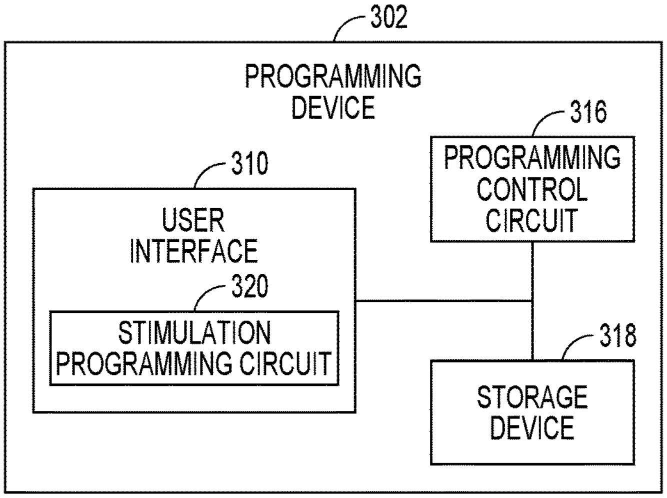
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation programming circuit 320. Storage device 318 stores information used by programming control circuit 316 and stimulation programming circuit 320, such as information about a stimulation device that relates the neurostimulation program to the plurality of stimulation parameters. In various embodiments, stimulation programming circuit 320 can be configured to support one or more functions allowing for programming of stimulation devices, such as stimulation device 104 including its various embodiments as discussed in this document, according to one or more selected neurostimulation programs and/or one or more algorithms for the closed-loop steering as discussed in the document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a “neurostimulation program” can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, “neurostimulation programming” can include the definition of the one or more stimulation waveforms, including the definition of one or more stimulation fields.

In various embodiments, circuits of neurostimulation system 100, including its various embodiments discussed in this document, may be implemented using a combination of hardware and software. For example, the circuit of user interface 110, stimulation control circuit 214, programming control circuit 316, and stimulation programming circuit 320, including their various embodiments discussed in this document, can be implemented using an application-specific circuit constructed to perform one or more particular functions and/or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
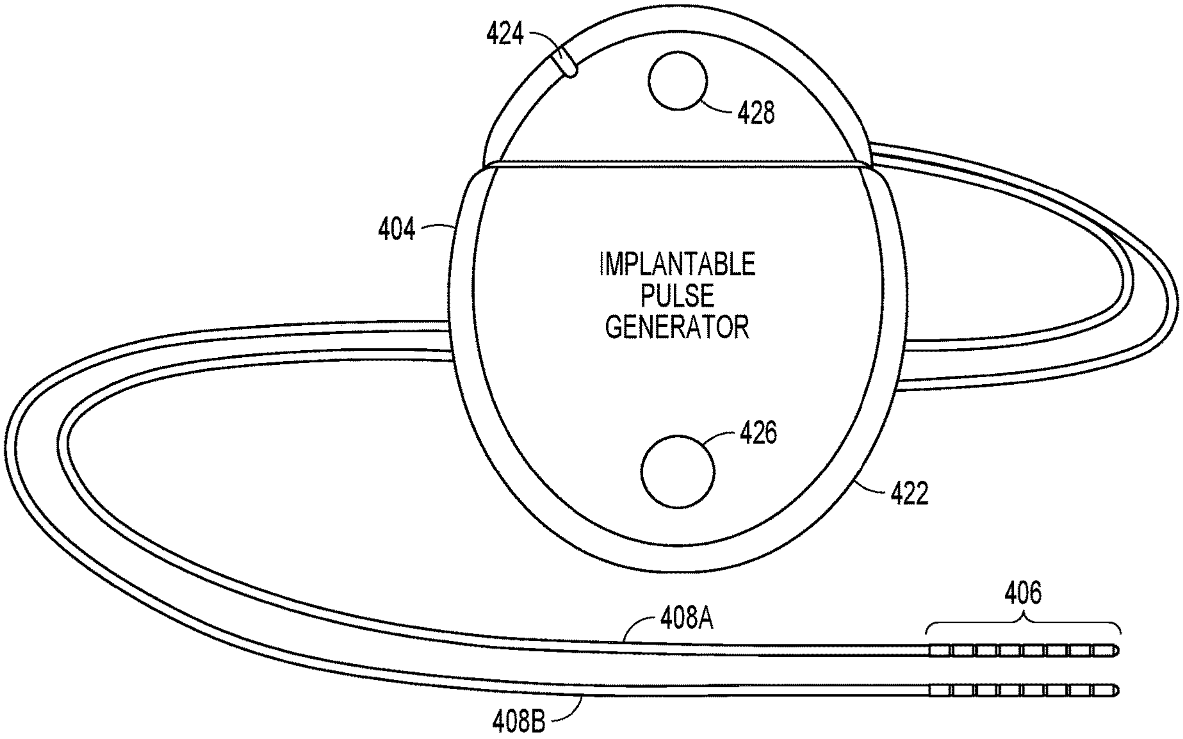
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrodes (also referred to as contacts) 406 for contacting a tissue site targeted for electrical neurostimulation. As illustrated in FIG. 4, leads 408A and 408B each include 8 electrodes 406 at the distal end. The number and arrangement of leads 408A and 408B and electrodes 406 as shown in FIG. 4 are only an example, and other numbers and arrangements are possible. In various embodiments, the electrodes are ring electrodes. In various embodiments applying DBS or SCS, the implantable leads and electrodes may be configured by shape and size to provide electrical neurostimulation energy to a neuronal target included in the patient’s brain or configured to provide electrical neurostimulation energy to target nerve cells in the patient’s spinal cord.

Figure 5:
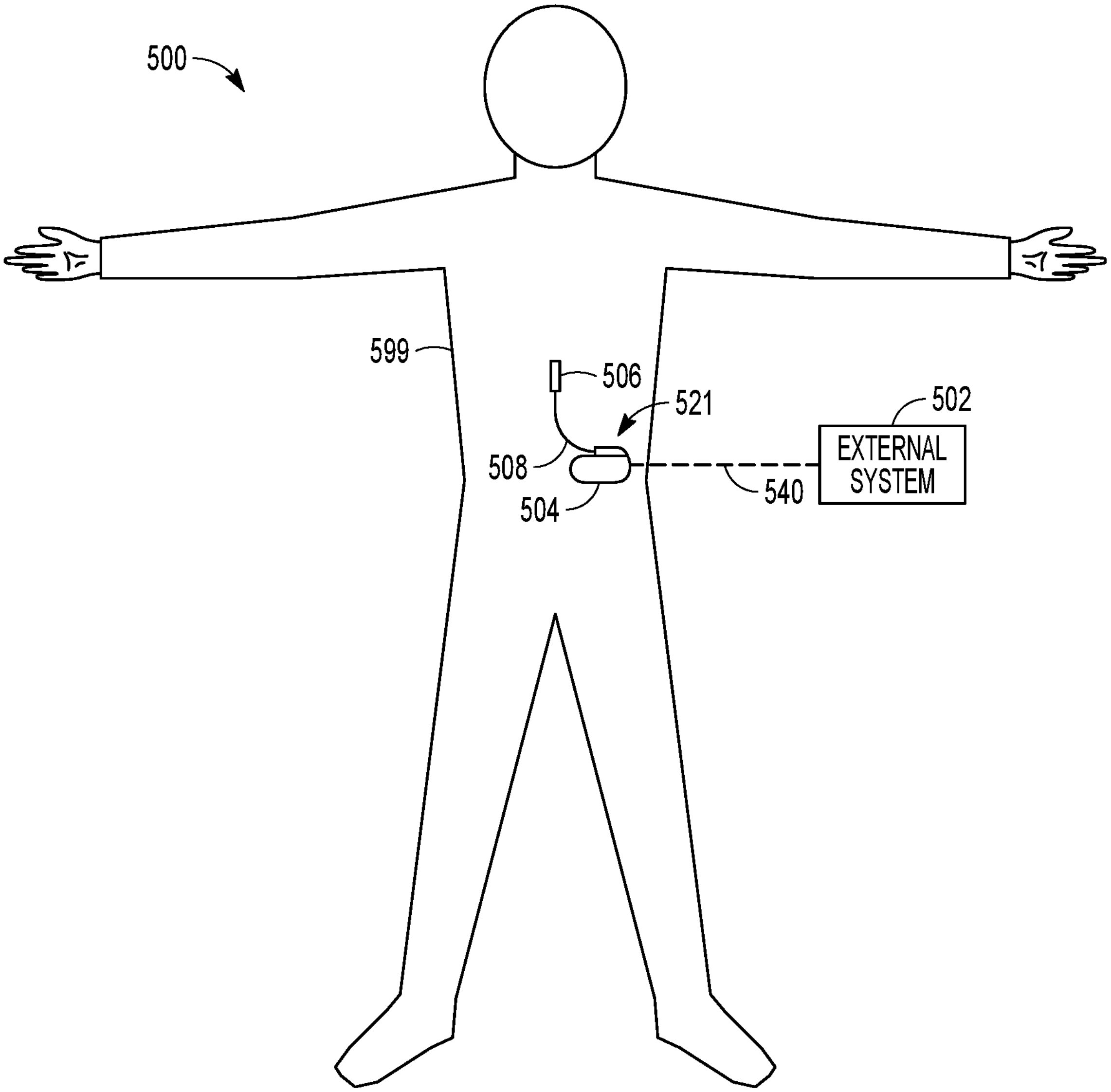
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient’s body 599.

Implantable system 521 includes an implantable stimulator (also referred to as an implantable pulse generator, or IPG) 504, a lead system 508, and electrodes (also referred to as contacts) 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and shapes of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient’s body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
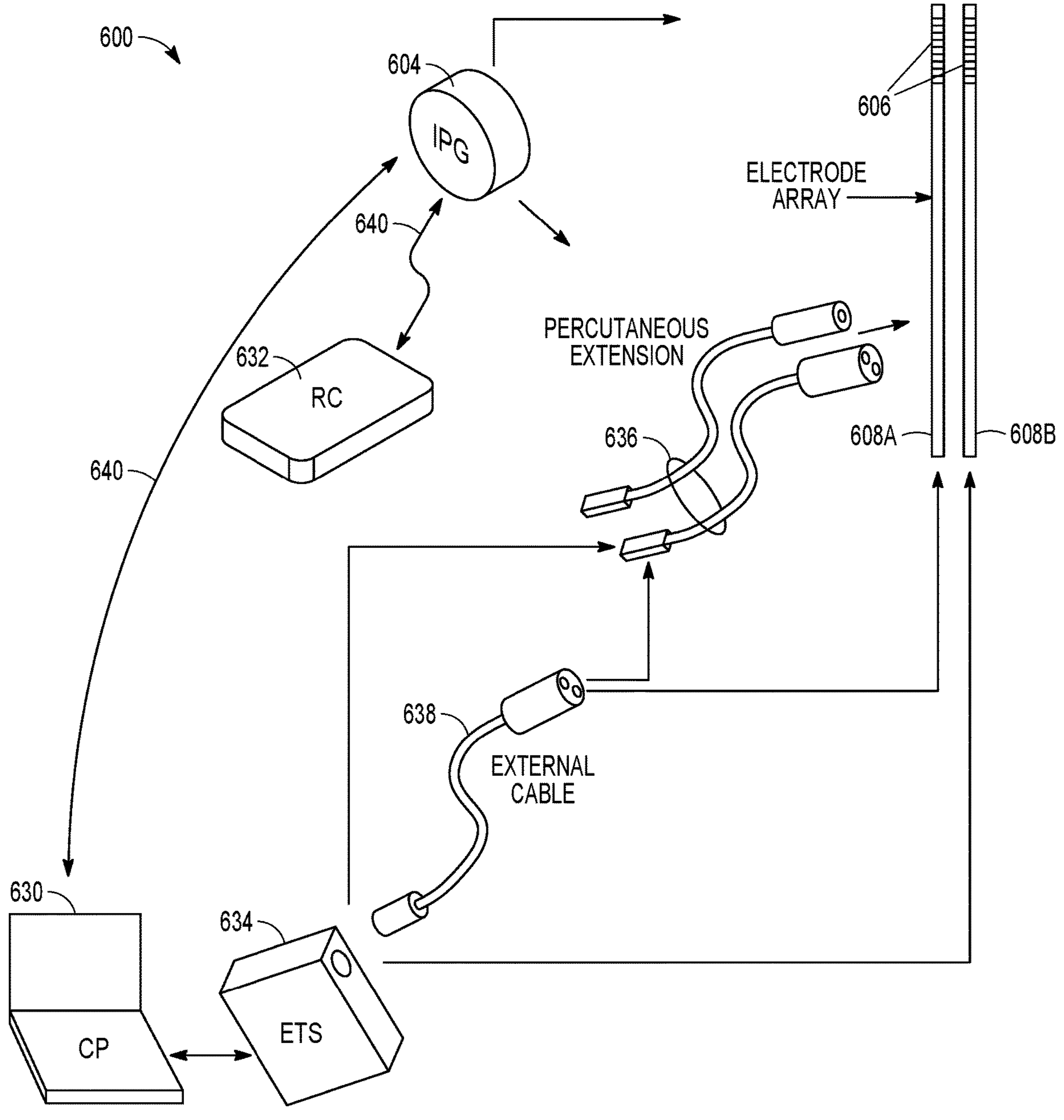
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, ETM) 634. IPG 604 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes (also referred to as contacts) 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$, is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 640. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632. In various embodiments, RC 632 can be a dedicated device or a general-purpose device configured to perform the functions of RC 632, such as a smartphone, a tablet computer, or other smart/mobile device.

Figure 7:
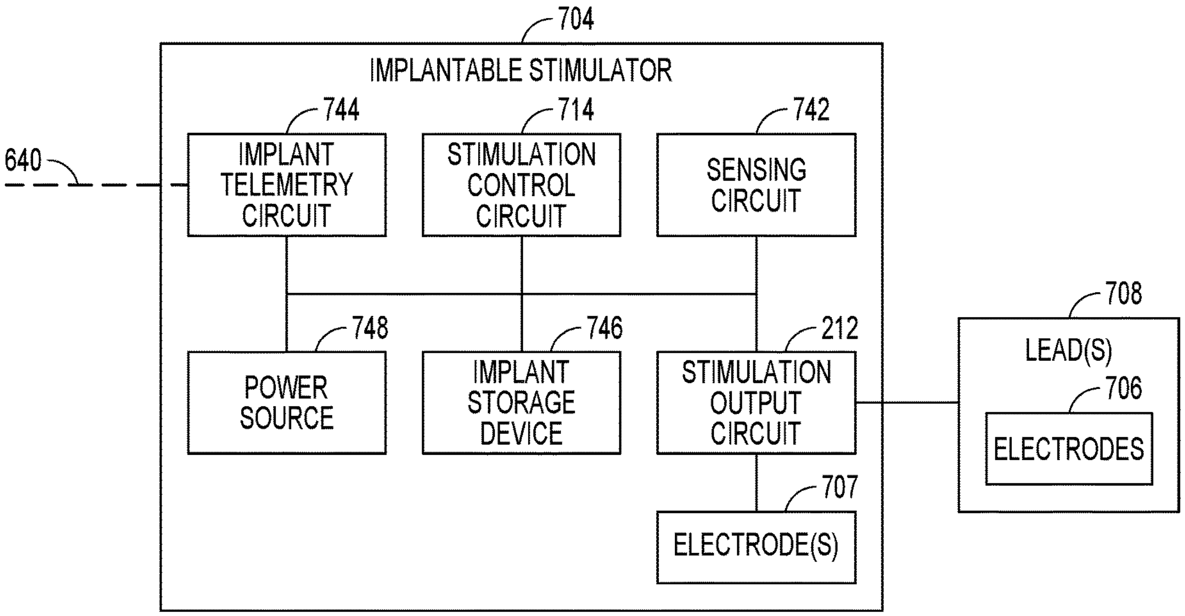
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes (also referred to as contacts) 706, which represents an example of electrodes 106 or 206 and may be implemented as electrodes 606.

Implantable stimulator 704 may include a sensing circuit 742 that provides the stimulator with a sensing capability, stimulation output circuit 212, a stimulation control circuit 714, an implant storage device 746, an implant telemetry circuit 744, a power source 748, and one or more electrodes 707. Sensing circuit 742 can one or more physiological signals for purposes of patient monitoring and/or feedback control of the neurostimulation. In various embodiments, sensing circuit 742 can sense one or more electrospinogram (ESG) signals using electrodes placed over or under the dura of the spinal cord, such as electrodes 706 (which can include epidural and/or intradural electrodes). In addition to one or more ESG signals, examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 (e.g., by installing a new application in a smart device such as a smartphone) and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
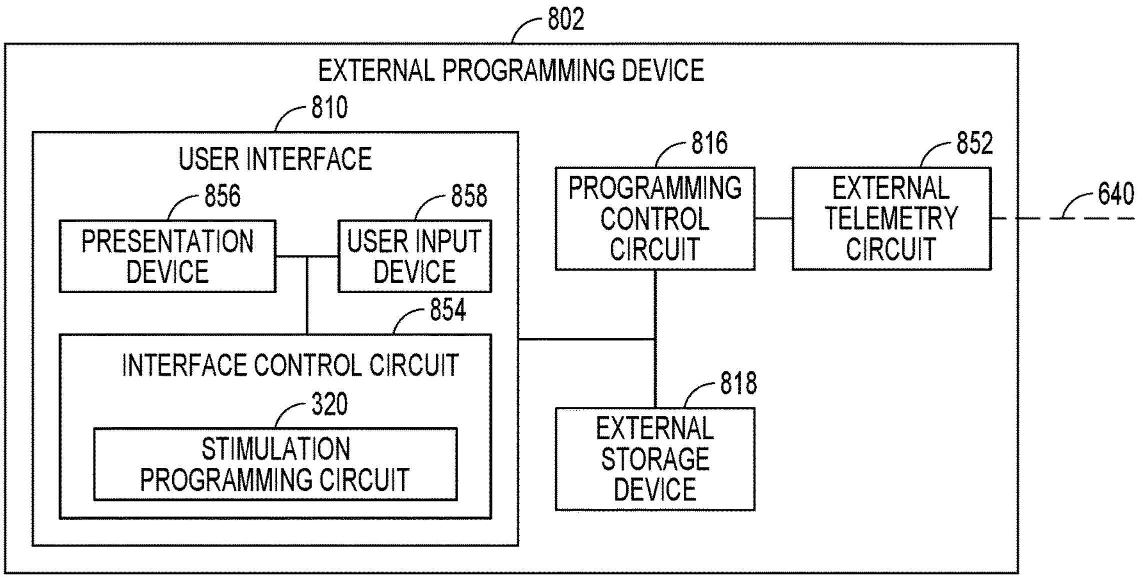
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). This can allow for patient mobility during programming and assessment when needed. For example, wireless communication link 640 can include at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS or SCS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g., mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation programming circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

FIGS. 9-16 illustrate examples of effects of the patient's body movements on neural responses during SCS. In various embodiments, a neural signal is sensed and used in closed-loop control of delivery of neurostimulation in which the patient's neural activation changes should be responded by adjusting one or more stimulation parameters. Changes in the sensed neural signal are used to indicate the patient's neural activation changes, but factors other than the neural activation changes can also affect the sensed neural signal. Such factors need to be excluded when determining whether a change in the sensed neural signal should trigger an adjustment of the stimulation parameter(s). A computational ECAP model of the spinal cord was used for studying the effects of the patient's body movements on neural responses using simulations. Examples of results produced by the simulation are shown in FIGS. 11 and 13-16.

Figure 9:
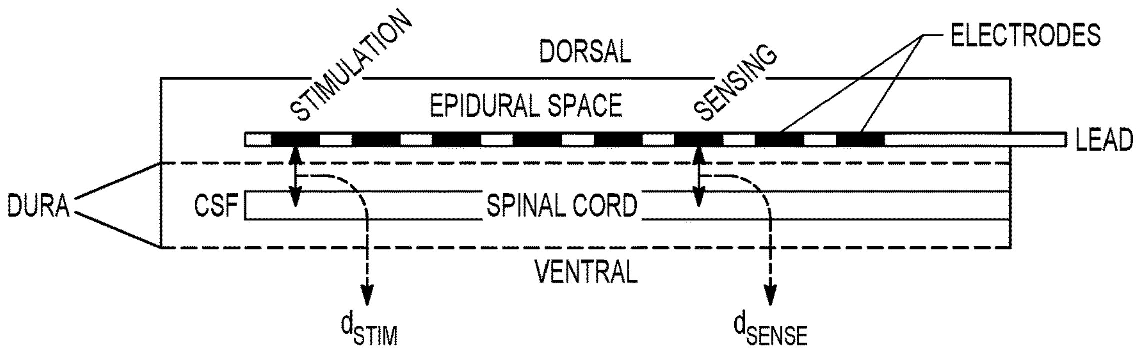
FIG. 9 illustrates an example of a lead including an electrode array placed over the spinal cord of a patient.

FIG. 9 illustrates an example of a lead including an array of electrodes placed over the spinal cord of a patient for delivering SCS to the patient. The spinal cord is in cerebrospinal fluid (CSF) surrounded by the dura mater (dura). The lead as shown in FIG. 9 has eight electrodes (also referred to as contacts) placed in the epidural space over the spinal cord. These electrodes can each be used as a stimulation electrode (though which neurostimulation is delivered to the patient) and/or a sensing electrode (through which a neural signal is sensed from the patient). FIG. 9 shows, as an example, that the first electrode from the left is used as a stimulation electrode, and the sixth electrode from the left is used as a sensing electrode. The distance between the stimulation electrode and the spinal cord is referred to as the stimulation distance ($d_{stim}$). The distance between the sensing electrode and the spinal cord is referred to as the sensing distance ($d_{sense}$). FIG. 9 shows an ideal case in which the stimulation distance and the sensing distance are equal ($d_{stim}=d_{sense}$) in the dorsal-ventral (DV) direction.

Figure 10A:
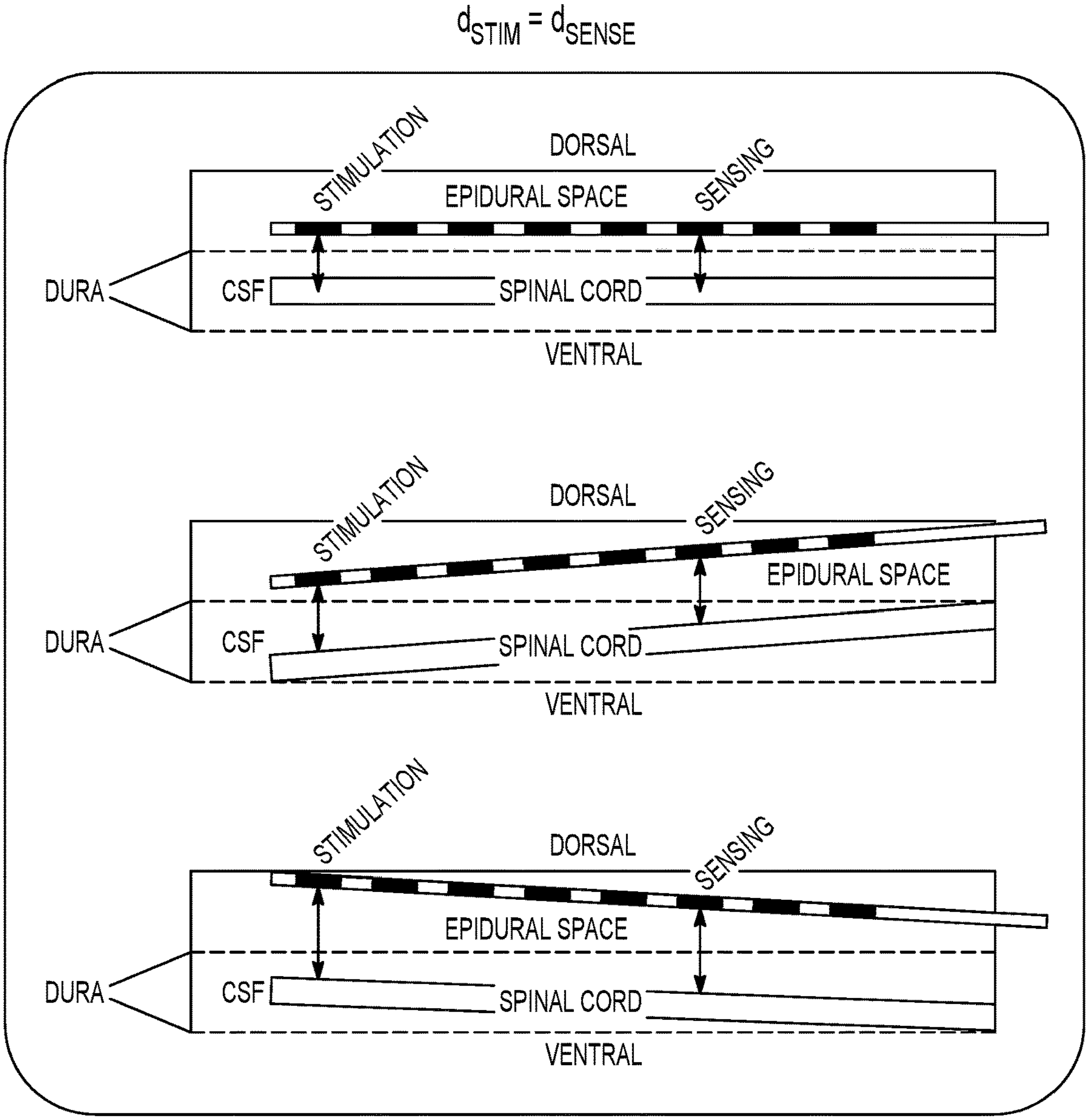
FIGS. 10A-10C illustrate various examples of displacement of the electrode array of FIG. 9 relative to the spinal cord, with FIG. 10A showing examples of equal stimulation and sensing distances, FIG. 10B showing examples of stimulation distance greater than sensing distance, and FIG. 10C showing examples of stimulation distance shorter than sensing distance.
Figure 10B:
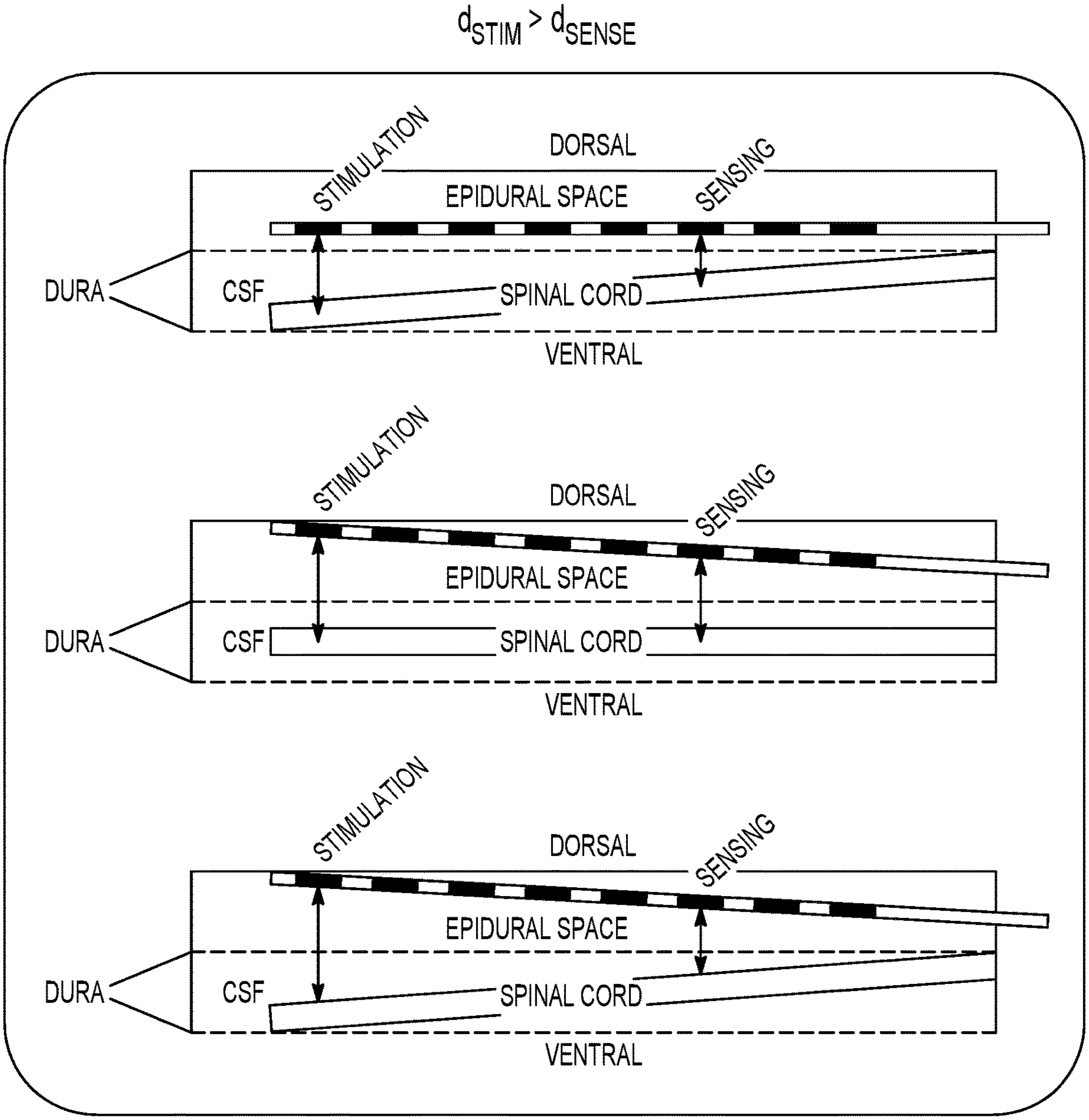
Figure 10C:
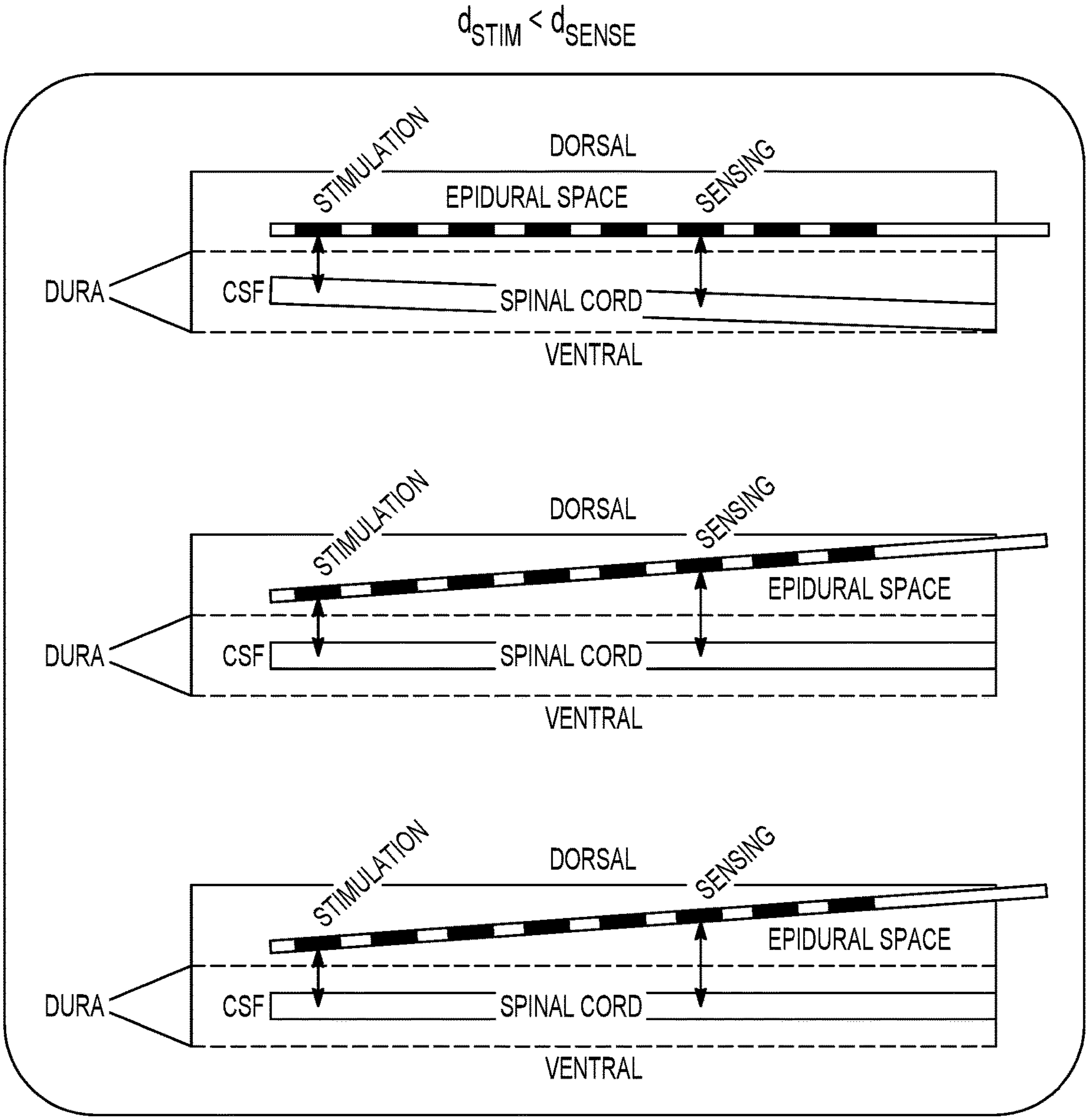

FIGS. 10A-10C illustrate various examples of displacement of the electrode array of FIG. 9 relative to the spinal cord. These examples illustrate various combinations of the stimulation distance and the sensing distance that may result from the patient's body movements. Such movements can cause the spinal cord to move within the CSF and/or the epidurally placed lead (including the sensing and stimulation electrodes to shift locations. The various combinations as illustrated in FIG. 10A includes cases of spinal cord movement and/or lead shifting resulting in substantially equal stimulation and sensing distances ($d_{stim}=d_{sense}$). FIG. 10B includes cases of spinal cord movement and/or lead shifting resulting in the stimulation distance substantially greater than the sensing distance ($d_{stim}>d_{sense}$). FIG. 10C include cases of spinal cord movement and/or lead shifting resulting in the stimulation distance substantially shorter than the sensing distance ($d_{stim}<d_{sense}$). All these combinations can be experiences in the practice of SCS.

Figure 11A:
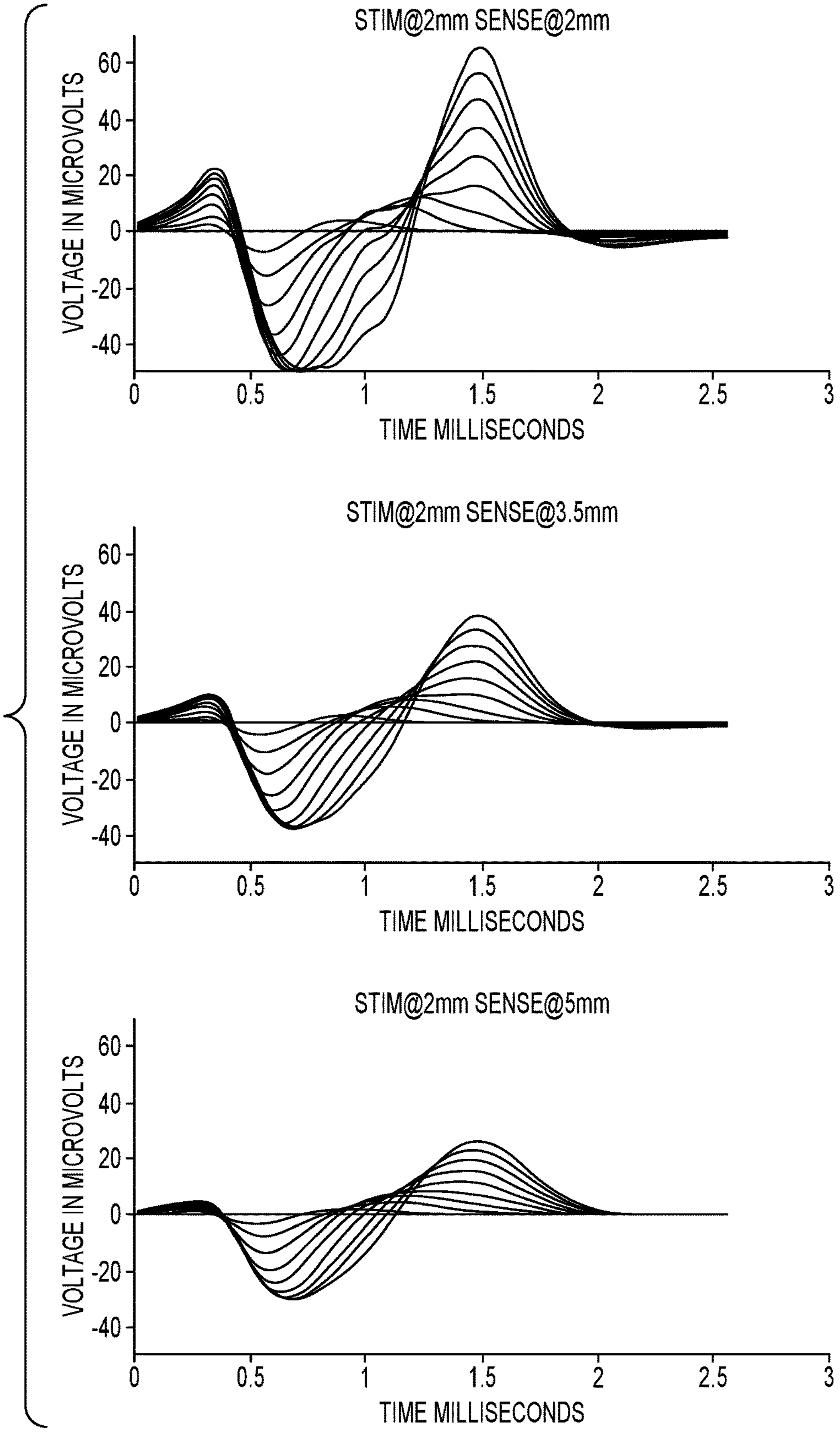
FIGS. 11A-11C illustrate various examples of neural responses to neurostimulation at various displacements of the electrode array of FIG. 9 relative to the spinal cord, with FIG. 11A showing examples with a fixed stimulation distance and a set of different sensing distances, FIG. 11B showing examples with another fixed stimulation distance and the set of different sensing distances, and FIG. 11C showing examples of yet another fixed stimulation distance and the set of different sensing distances.
Figure 11B:
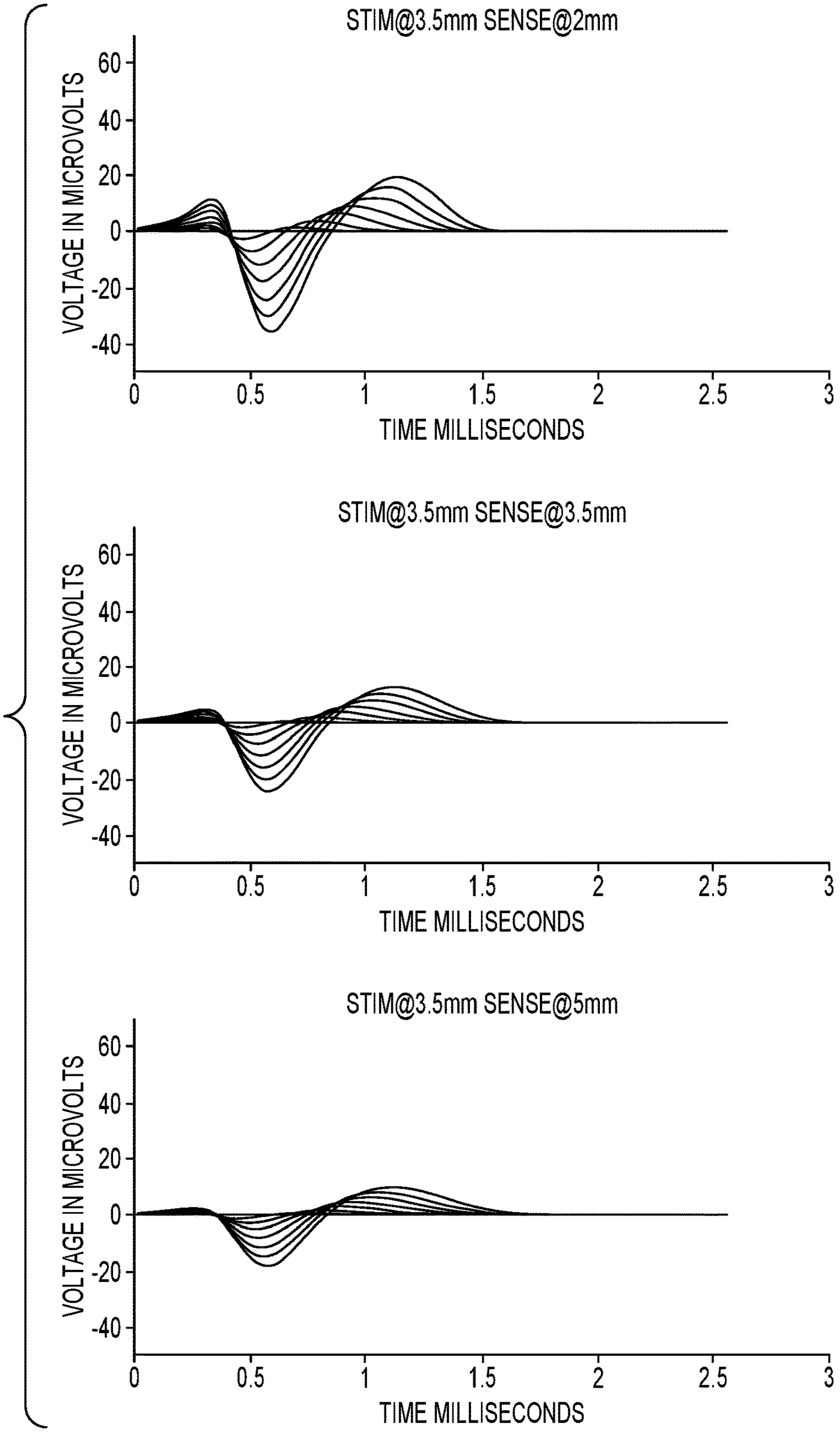
Figure 11C:
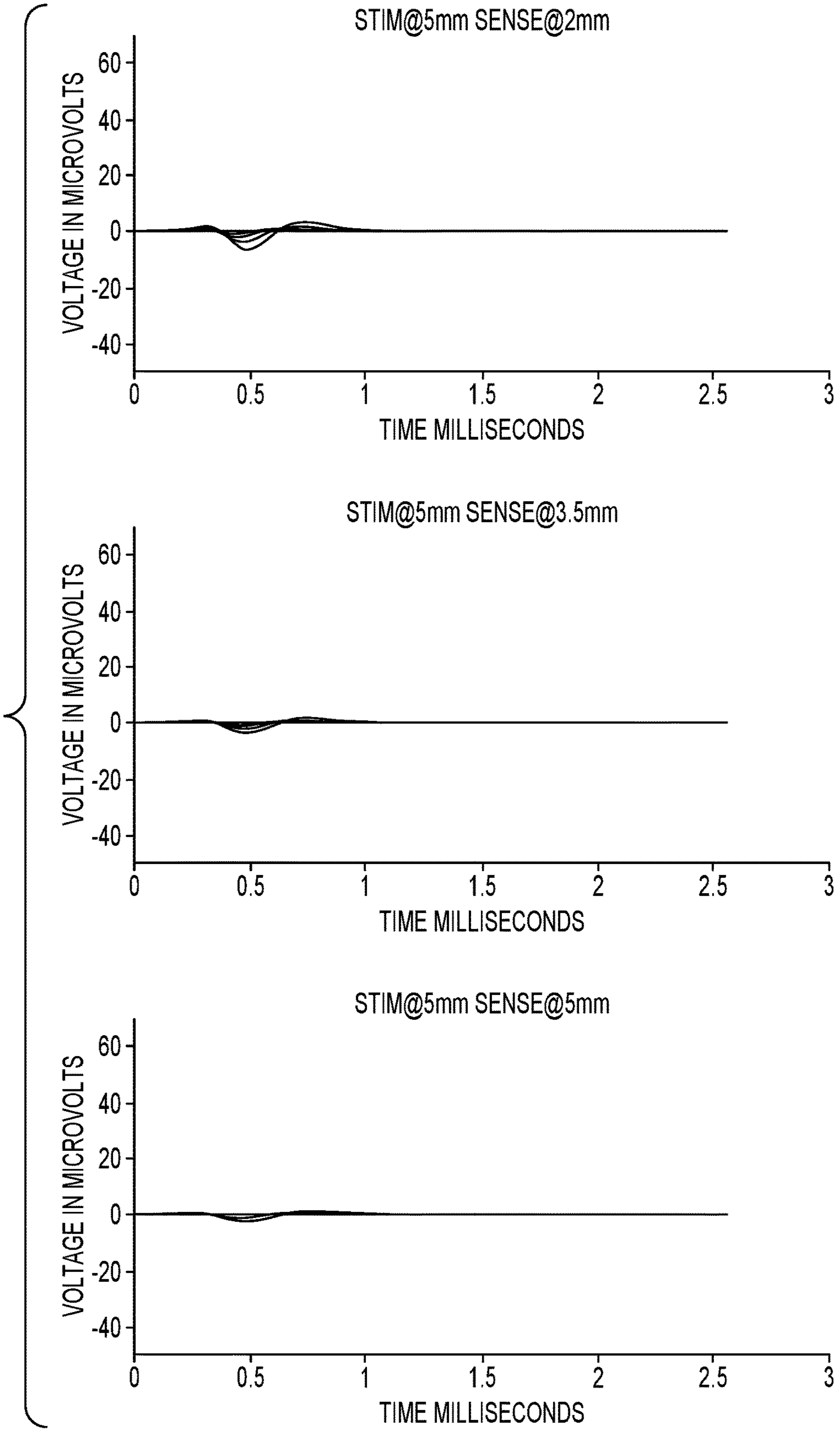

FIGS. 11A-11C illustrate various examples of neural responses to neurostimulation at various displacements of the electrode array of FIG. 9 relative to the spinal cord with FIG. 11A showing examples with a fixed stimulation distance and a set of different sensing distances, FIG. 11B showing examples with another fixed stimulation distance and the set of different sensing distances, and FIG. 11C showing examples of yet another fixed stimulation distance and the set of different sensing distances. These examples show sensed neural responses including ECAPs with different values of the stimulation distance and the sensing distance ("Stim@Xmm Sense@Ymm" means $d_{stim}$=X mm and $d_{sense}$=Y mm). The significant morphological differences in these sensed neural responses suggest that morphological features of the neural response (including ECAP features) in the sensed neural signal can be used to indicate changes in the sensed signal that attribute to changes in the stimulation distance and/or the sensing distance (rather than changes attributing to neural activation change).

Figure 12:
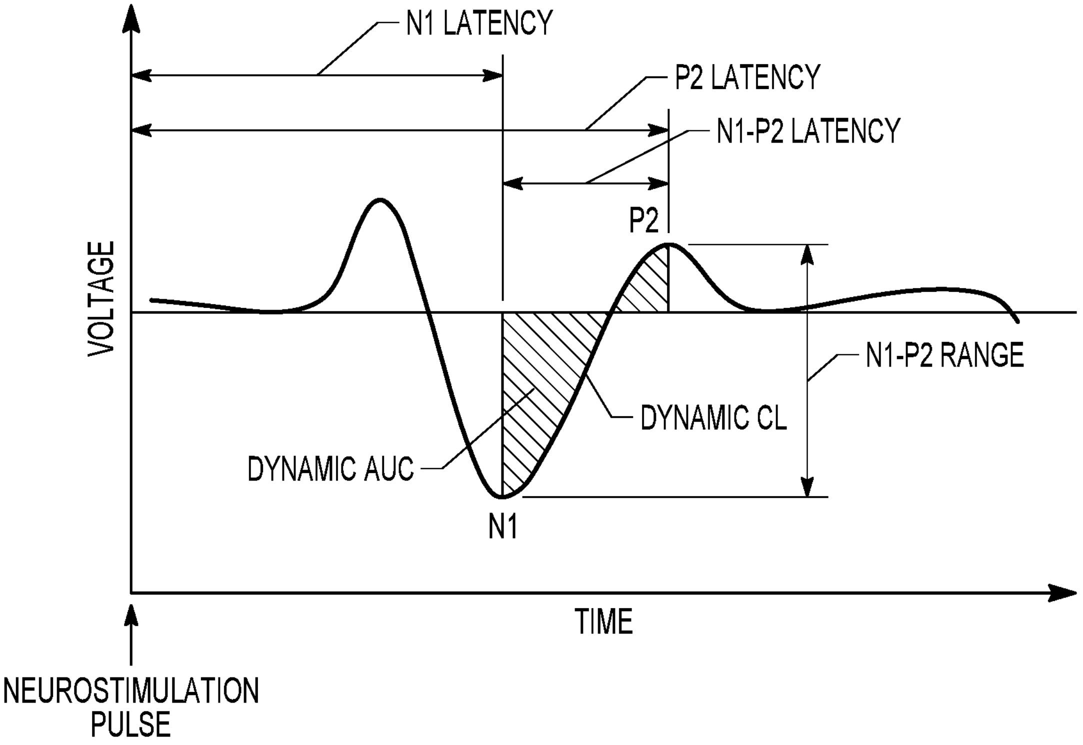
FIG. 12 illustrates examples of evoked compound action potential (ECAP) features of a neural signal and examples of neural response parameters produced using the ECAP features.

FIG. 12 illustrates examples of ECAP features of a neural signal and examples of neural response parameters produced using the ECAP features. The signal shown in FIG. 12 is an example of a neural response that is evoked by a neurostimulation pulse and includes an ECAP indicative of dorsal column response (e.g., as seen on an electrospinographic signal). Morphological features of the ECAP (herein referred to as "ECAP features") that can be used in the present subject matter include, but are not limited to:

N1: the first negative peak in an evoked response that is correlated to the response of faster fibers such as Aβ fibers and myelinated fibers; and P2: the second positive peak in the evoked response that is correlated with response of slower fibers.

Various neural response parameters can be derived from characteristics of the evoked responses as seen on the neural signal. In various embodiments, the one or more neural response parameters can be measured from the neural signal using the ECAP features. Examples of the one or more neural response parameters generated by detecting and measuring ECAP features for analyzing neural activation and/or controlling delivery of neurostimulation include:

N1-P2 latency: time between N1 and P2;

N1 latency: time interval between start of recording frame (e.g., the neurostimulation pulse) and N1;

P2 latency: time interval between start of recording frame (e.g., the neurostimulation pulse) and P2;

N1-P2 range: N1 to P2 amplitude (the difference between amplitudes of N1 and P2);

Dynamic curve length (CL): curve length measured from the sensed neural signal between N1 and P2; and Dynamic area under the curve (AUC): the area between the sensed neural signal and a baseline, measured between N1 and P2.

In addition to or in place of the time-domain parameters above, the one or more neural response parameters can also include, for example:

Spectral power parameters (e.g. peak amplitude of each ECAP feature and/or total AUC of ECAP power band from 500 Hz to 3000 Hz);

Parseval power parameters (integral of the spectrum squared over a relevant power band); and Other metrics of energy or power.

In various embodiments, one or more of these neural response parameters can be used in the analysis distinguishing changes in the sensed neural signal caused by the patient's body movements from true neural activation changes. While the ECAP features and neural response parameters illustrated in FIG. 12 are discussed as examples, other ECAPs and neural response parameters can be suitable and used in the present subject matter as determined by those skilled in the art.

Figure 13:
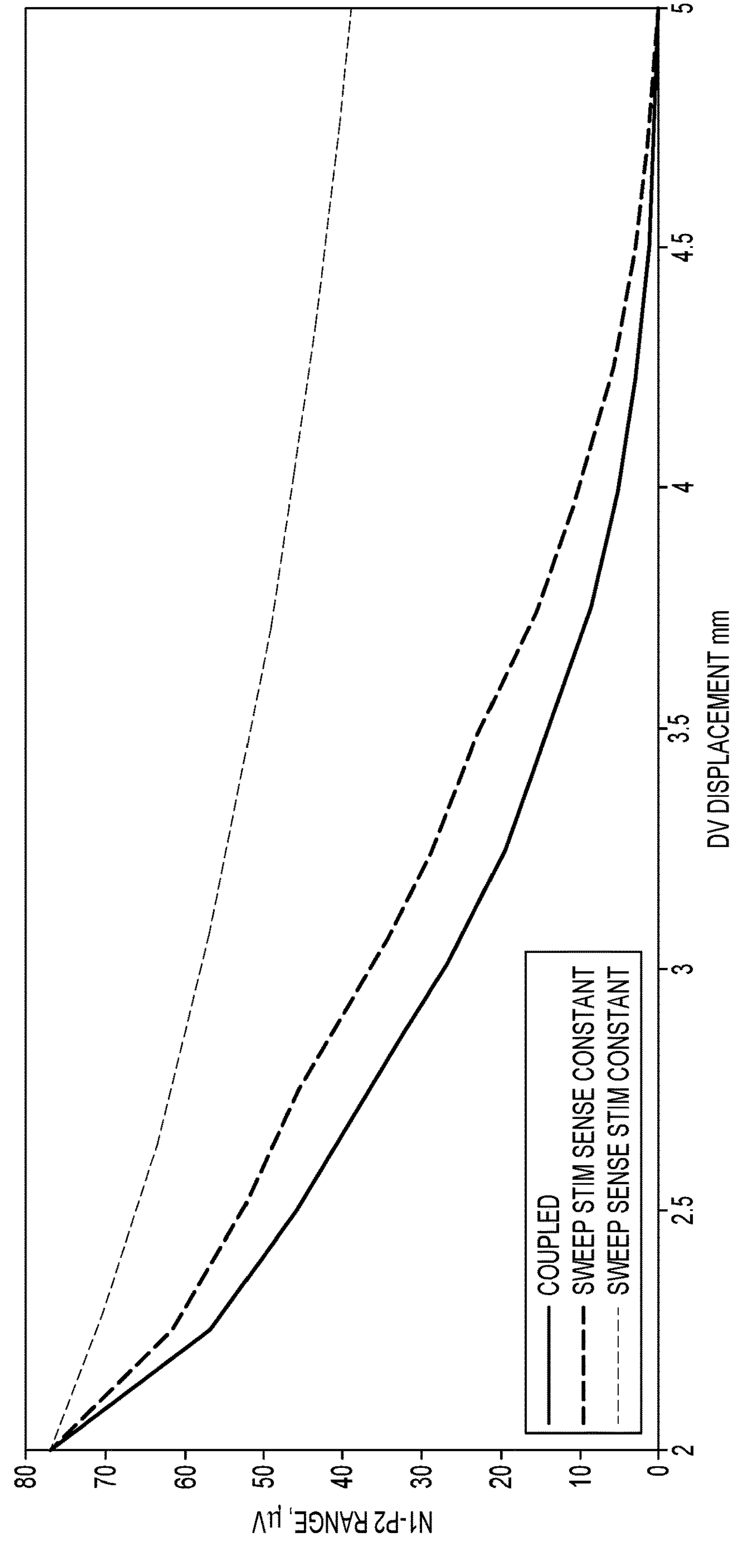
FIG. 13 illustrates an example of a neural response parameter plotted as a function of distances between electrodes and the spinal cord.

FIG. 13 illustrates an example of a neural response parameter plotted as a function of distances between electrodes and the spinal cord. The neural response parameter shown in FIG. 13 include curves of N1-P2 range each plotted as a function of DV stimulation distance (stimulation distance measured in the DV direction) and/or DV sensing distance (sensing distance measured in the DV direction) change. When the stimulation electrode and the sensing electrodes shift by the same amount ("Coupled", i.e., with the stimulation distance and the sensing distance remaining equal), a neural activation change is expected and the stimulation current should be adjusted as a response. When the stimulation distance is swept while keeping the sensing distance constant ("Sweep Stim Sense Constant"), a neural activation change is expected and the stimulation current should be adjusted as a response. When the sensing distance is swept while keeping the stimulation distance constant ("Sensing Sweep Stim Constance), a neural activation change is not expected, and the stimulation current should not be adjusted as a response.

Figure 14:
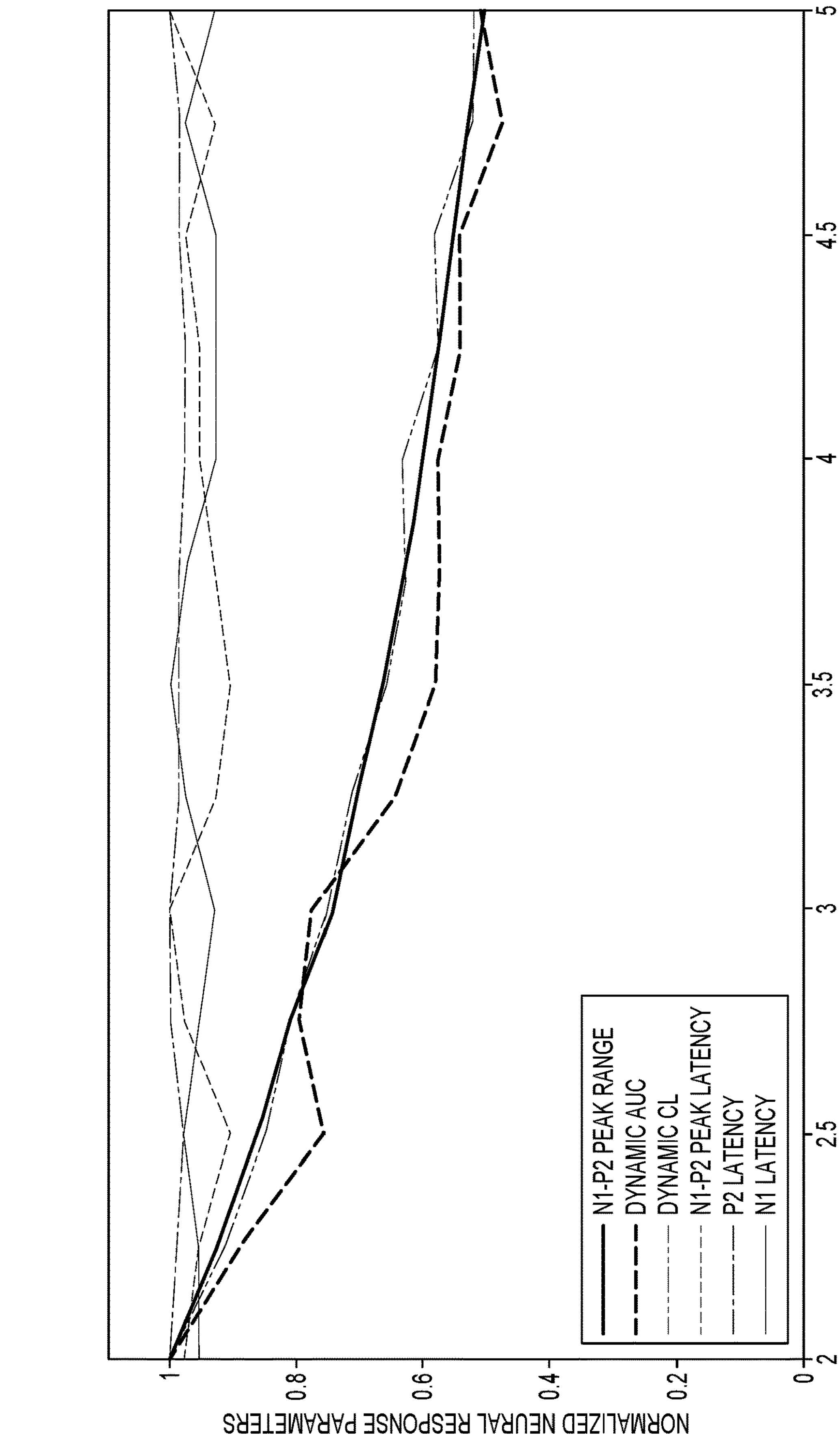
FIG. 14 illustrates an example of normalized neural response parameters each plotted as a function of the distance between a sensing electrode and the spinal cord.

FIG. 14 illustrates an example of normalized neural response parameters each plotted as a function of the distance between the sensing electrode and the spinal cord. Six normalized neural response parameters are shown in FIG. 14 each as a function of the DV sensing distance, as the DV sensing distance is swept when the DV stimulation distance is held constant at 2 mm (with addition of a 0.5 mA RMS noise floor to make the effects more visible, and the stimulation current set to 4.3 mA), When sweeping across various DV sensing distances, the latency parameters (i.e., N1 latency, N1-P2 latency, and P2 latency) do not change significantly. This is as predicted because changing the sensing distance without changing the stimulation distance is expected to change the amplitude of the sensed neural signal without substantially changing timing characteristics of the sensed neural signal. The other neural response parameters, including N1-P2 range, dynamic AUC, and dynamic CL change significantly. With the stimulation distance kept constant, changes in the sensing distance only affect how the neural response signal is sensed, without actually affecting the patient's neural activation. The stimulation current should not be adjusted.

Figure 15:
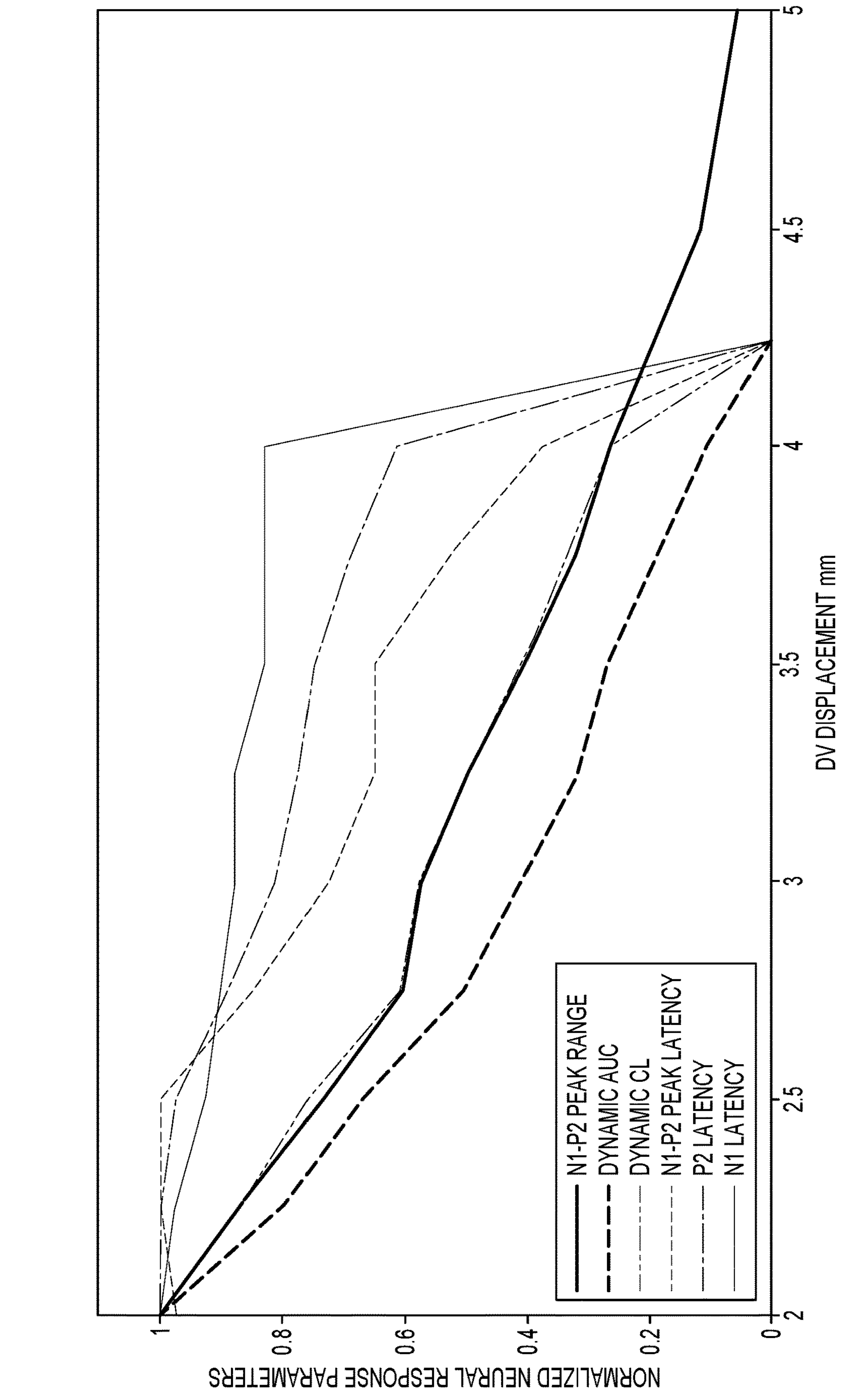
FIG. 15 illustrates an example of normalized neural response parameters each plotted a function of the distance between a stimulation electrode and the spinal cord.

FIG. 15 illustrates an example of normalized neural response parameters each plotted a function of the distance between the stimulation electrode and the spinal cord. The same six normalized neural response parameters as shown in FIG. 14 are shown in FIG. 15 each as a function of the DV stimulation distance, as the DV stimulation distance is swept when the DV sensing distance is held constant at 2 mm (with addition of a 0.5-mA RMS noise floor to make the effects more visible; note the sharp taper is caused by the ECAP falling below the noise floor, and the stimulation current set to 4.3 mA). When sweeping across various DV stimulation distances, the latency parameters (i.e., N1 latency, N1-P2 latency, and P2 latency) change more significantly, but not in such a way that is suitable for feedback control (i.e., cannot simply use one or more latency parameters for running the ECAP-based closed-loop control algorithm). This is as predicted because changing the stimulation distance without changing the sensing distance is expected to change the neural activation and hence the sensed neural signal including the ECAP features. The other neural response parameters, including N1-P2 range, dynamic AUC, and dynamic CL change significantly. With the sensing distance kept constant, the effect of changes in the stimulation distance on the actual neural responses is reflected in the sensed neural signal. The stimulation current should be adjusted.

Figure 16:
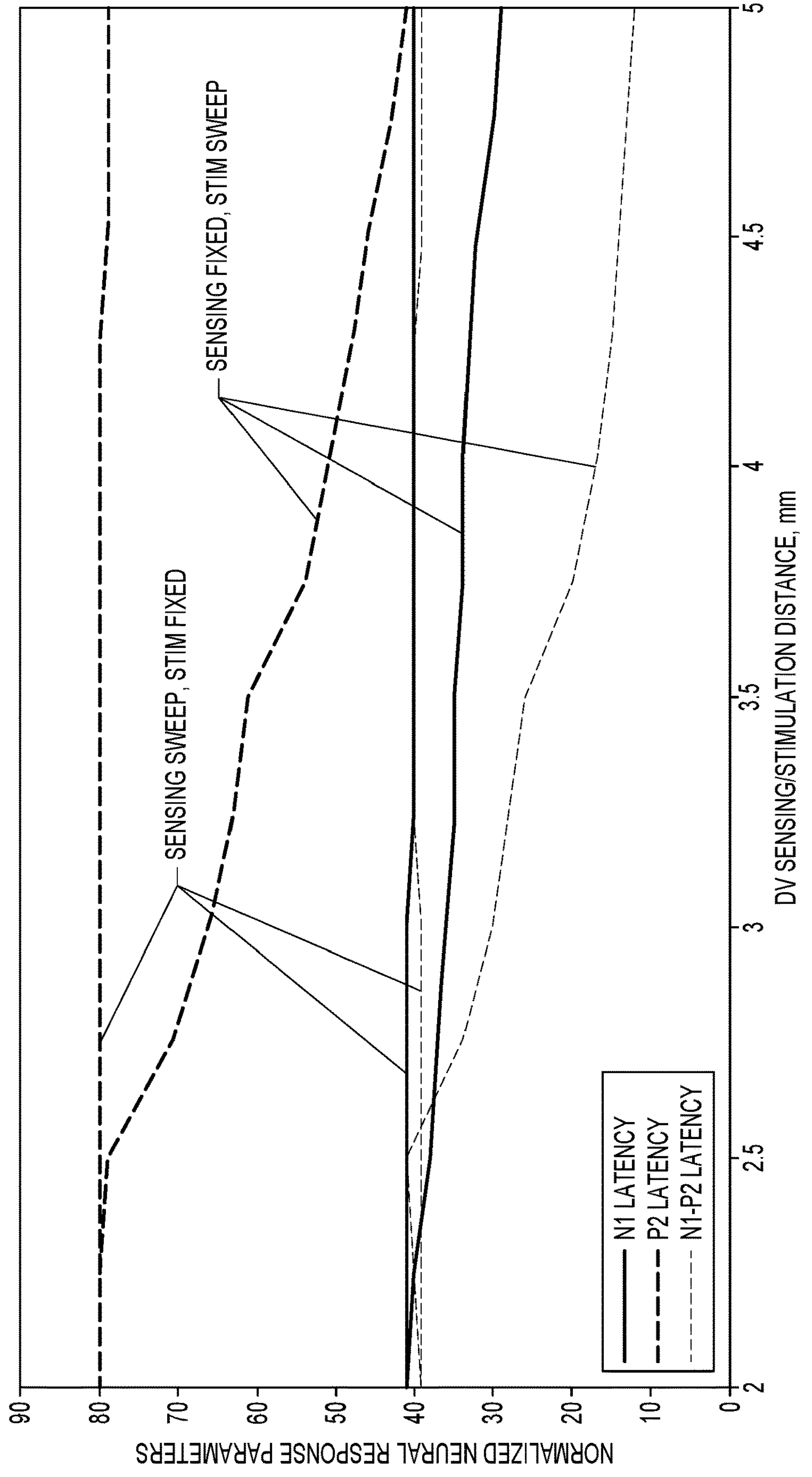
FIG. 16 illustrates an example of normalized neural response parameters each plotted as the function of the distance between the sensing electrode and the spinal cord and plotted as the function of the distance between the stimulation electrode and the spinal cord.

FIG. 16 illustrates an example of normalized neural response parameters each plotted as the function of the distance between the sensing electrode and the spinal cord and plotted as the function of the distance between the stimulation electrode and the spinal cord. The normalized latency parameters (i.e., N1 latency, N1-P2 latency, and P2 latency) (without addition of a noise floor) are shown in FIG. 16 each plotted as a function of the DV stimulation distance (when the DV sensing distance is held constant and the stimulation current should be adjusted) and plotted as a function of the DV sensing distance (when the DV stimulation distance is held constant and the stimulation current should not be adjusted). When the latency parameters are compared with each other, the P2 Latency has the largest difference between the function of the DV stimulation distance and the function of the DV sensing distance. While being an example rather than a restriction or conclusion, this suggests how a neural response parameter can be identified for use in an algorithm analyzing one or more neural response parameters to determine true neural activation changes.

From the results of the simulation using the computational ECAP model of the spinal cord, no neural response parameter derived from the ECAP features was found suitable for use in the closed-loop control algorithm while being insignificantly affected by the patient's body movements and factors other than neural activation change. However, one or more neural response parameters can be identified for use in an analysis determining whether a change detected from the sensed neural signal results from an actual neural activity change. Using an analysis of such one or more neural response parameters, a closed-loop control algorithm for controlling delivery of neurostimulation can be made substantially insensitive to changes in the sensed neural signal resulting from factors other than neural activation changes using characteristics of the ECAP features. Thus, the present system analyzes changes in the sensed neural signal using the one or more neural response parameters to determine whether an actual neural activity change has occurred when one or more stimulation parameters are to be adjusted only in response to an actual neural activity change. Examples of such analysis and their use in a neurostimulation system are discussed below.

Figure 17:
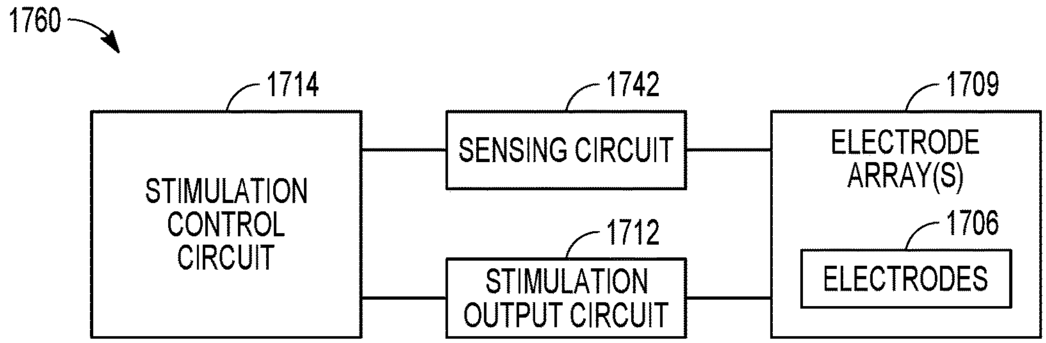
FIG. 17 illustrates an embodiment of a system for delivering neurostimulation with closed-loop control using a sensed neural signal, such as may be implemented in the neurostimulation system of FIG. 1.

FIG. 17 illustrates an embodiment of a system 1760 for delivering neurostimulation with closed-loop control using a sensed neural signal. System 1760 includes one or more electrode arrays 1709 including a plurality of electrodes (as referred to as contacts) 1706, a stimulation output circuit 1712, a sensing circuit 1742, and a stimulation control circuit 1714. Electrode array(s) 1709 can include electrodes on one or more leads. As an example, FIGS. 9 and 10 show a lead including an electrode array of eight electrodes, with one used as a stimulation electrode and another used as a sensing electrode. Stimulation output circuit 1712 can deliver the neurostimulation using a stimulation electrode selected from electrodes 1706. Sensing circuit 1742 can sense a neural signal indicative of neural responses using a sensing electrode selected from electrodes 1706. The neural responses are each a response to the delivery of the neurostimulation. In various embodiments, the neurostimulation includes neurostimulation pulses, and the neural responses are each evoked by a pulse of the neurostimulation pulses. In various embodiments, the neural responses include ECAPs each evoked by a pulse of the neurostimulation pulses. Stimulation control circuit 1714 can control the delivery of the neurostimulation using the sensed neural signal and a plurality of stimulation parameters according to a closed-loop control algorithm. In various embodiments, stimulation control circuit 1714 can be configured (e.g., programmed) to execute a stimulation-adjustment algorithm to adjust a dynamically controlled stimulation parameter of the plurality of stimulation parameter using the sensed neural signal and an outcome of analyzing changes in the neural response. The dynamically controlled stimulation parameter is a stimulation parameter that is adjusted as a result of executing the closed-loop control algorithm.

System 1760 can be implemented in neurostimulation systems such as systems 100, 500, and 600. In various embodiments, system 1760 can be implemented in an implantable medical device, such as IPG 404, IPG or implantable stimulator 504, IPG 604, or implantable stimulator 704, and an external programming device, such as external system 502, CP 630, RC 632, or external programming device 802, as discussed in this document. For example, when system 1760 is implemented in implantable stimulator 704 and external programming device 802, lead(s) 708 can include electrode array(s) 1709 including electrodes 1706, stimulation output circuit 212 can be configured to include stimulation output circuit 1712, sensing circuit 742 can be configured to include sensing circuit 1742, stimulation control circuit 714 can be configured to include stimulation control circuit 1714, and stimulation programming circuit 320 can be configured to supporting programming of implantable stimulator 704 for the operations of system 1760. In various embodiments, system 1760 can be implemented in a single implantable or non-implantable neurostimulator with parameters needed for its operation programmable using a programming device.

Figure 18:
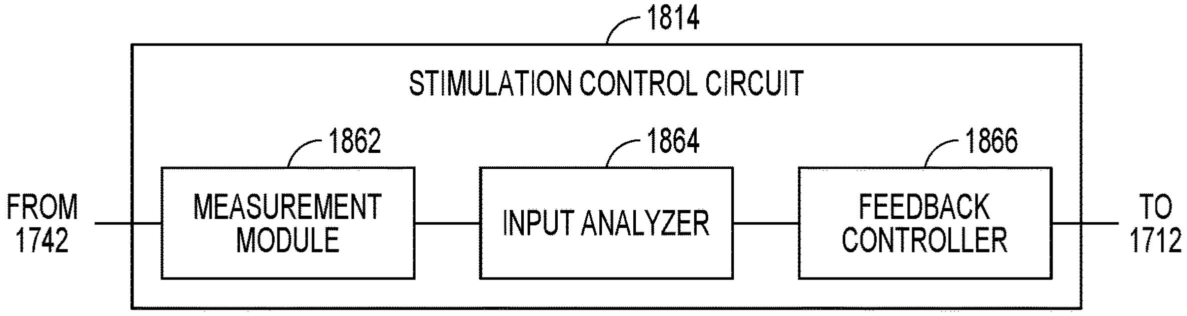
FIG. 18 illustrates an embodiment of a stimulation control circuit of a neurostimulation system, such as the system of FIG. 17.

FIG. 18 illustrates an embodiment of a stimulation control circuit 1814, which can represent an example of stimulation control circuit 1714. Stimulation control circuit 1814 includes a measurement module 1862, an input analyzer 1864, and a feedback controller 1866.

Measurement module 1862 can detect morphological features of the neural responses and produce a neural response parameter using the detected morphological features. The morphological features can include ECAP features each being a morphological feature of the ECAPs, and measurement module 1862 can detect the ECAP features and measure the neural response parameter using the detected ECAP features. In various embodiments, the neural response parameter is directly measured from one or more of the detected ECAP features or a function of the directly measured value. In various other embodiments, the neural response parameter is a combination (e.g., a function, including a weighted function) of multiple neural response parameters each directly measured from one or more of the detected ECAP features.

Input analyzer 1864 can detect a change in the sensed neural signal and analyze the produced neural response parameter for attributing the detected change to a neural activation change in the patient or a body movement of the patient. In various embodiments, input analyzer 1864 determines whether the detected change indicates a neural activation change has occurred. In various other embodiments, input analyzer 1864 produces a parameter (e.g., a weighting factor) as a function of the neural response parameter. The value of that parameter indicates whether a neural activation change has occurred.

Feedback controller 1866 can control the dynamically controlled stimulation parameter according to the closed-loop control algorithm using the sensed neural signal and an outcome of the analysis performed by input analyzer 1864. The outcome of the analysis indicates the neural activation change has occurred or a likeliness of occurrence of the neural activation change. In various embodiments, feedback controller 1866 adjusts the dynamically controlled stimulation parameter in response to a determination that the neural activation change has occurred and does not adjust the dynamically controlled stimulation parameter (i.e., keeps the dynamically controlled stimulation parameter unchanged) if the determination is that the neural activation change has not occurred. In various embodiments, feedback controller 1866 adjusts the dynamically controlled stimulation parameter after applying the parameter being the function of the neural response parameter and indicating whether a neural activation change has occurred, such as after applying the weighting factor to the dynamically controlled stimulation parameter.

Figure 19:
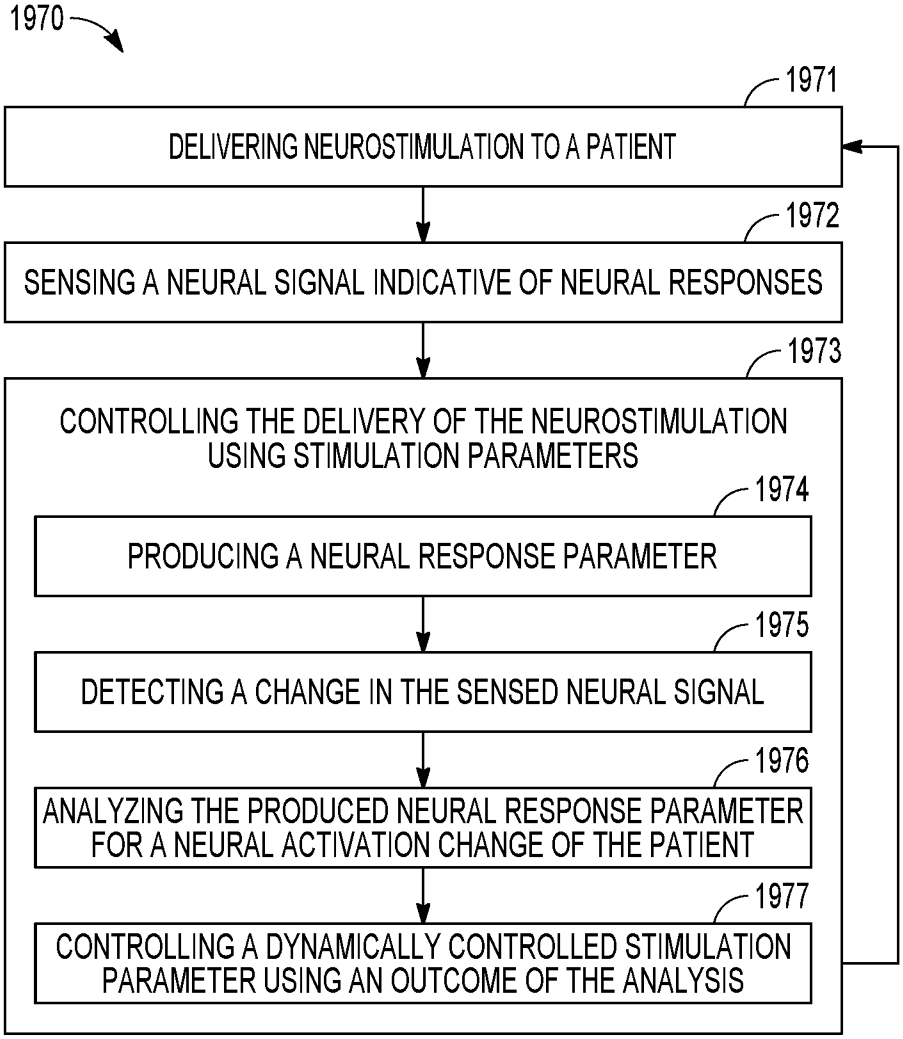
FIG. 19 illustrates an embodiment of a method for delivering neurostimulation with closed-loop control using a sensed neural signal with determination of true neural activation changes indicated in the sensed neural signal.

FIG. 19 illustrates an embodiment of a method 1970 for delivering neurostimulation to a patient with closed-loop control using a sensed neural signal with determination of true neural activation changes indicated in the sensed neural signal. System 1760 can be configured for performing method 1970. A non-transitory computer-readable storage medium can include instructions, which when executed by a system, such as system 1760, cause the system to perform method 1970. In one example, the instructions are included in implant storage device 746, to be executed by implantable stimulator 704 using a processor of stimulation control circuit 714.

At 1971, the neurostimulation is delivered to the patient (e.g., from stimulation output circuit 1712 through a stimulation electrode selected from electrodes 1706. At 1972, a neural signal indicative of neural responses is sensed (e.g., using sensing circuit 1742 through a sensing electrode selected from electrodes 1706). The neural responses are each a response to the delivery of the neurostimulation. At 1973, the delivery of the neurostimulation is controlled using a plurality of stimulation parameters (e.g., using a processor of system 1760 that includes portions of stimulation control circuit 1714 or 1814). The control can include steps 1974, 1975, 1976, and 1977, among other things.

At 1974, a neural response parameter is produced. This can include detecting morphological features of the neural responses and producing the neural response parameter using the detected morphological features. Examples of the morphological features includes the ECAP features (e.g., N1 and P2), and examples of the neural responses parameters can include neural response parameters measured and/or calculated from one or more ECAP features (e.g., N1-P2 latency, N1 latency, P2 latency, N1-P2 range, dynamic CL, dynamic AUC, or any combination of these parameters), as discussed above (e.g., with reference to FIG. 12). At 1975, a change in the sensed neural signal is detected. At 1976, the neural response parameter produced at 1974 is analyzed for attributing the detected change to one of a neural activation change in the patient or a body movement of the patient. At 1977, a dynamically controlled stimulation parameter of the plurality of stimulation parameters is controlled an outcome of the analysis. In various embodiments, in response to the outcome of the analysis indicating the neural activation change, the dynamically controlled stimulation parameter is adjusted using the sensed neural signal according to a closed-loop control algorithm. If the outcome of the analysis indicates no the neural activation change has occurred, the dynamically controlled stimulation parameter is kept unchanged.

In various embodiments, method 1970 is performed by executing a stimulation-adjustment algorithm (e.g., by configuring system 1976 for executing the stimulation-adjustment algorithm in addition to, or as part of, executing the closed-loop control algorithm). Various examples of the stimulation-adjustment algorithm are discussed below, with references to FIGS. 20-23

Stimulation-Adjustment Algorithm Examples

Examples 1-4 are each discussed below as an example of an algorithm implementing method 1970. In each example of Examples 1-4, the stimulation-adjustment algorithm is executed while the neurostimulation is being delivered and the neural signal including neural responses to the delivery of the neurostimulation is sensed. The neurostimulation includes neurostimulation pulses. The neural responses include ECAPs each evoked by a pulse of the neurostimulation pulses.

In each example of the Examples 1-4:

the "neural response parameter" can be a measured neural response parameter (e.g., directed measured using one or more ECAP features) or calculated as a function (including a weighted function) of one or more measured neural response parameters (e.g., each directly measured using one or more ECAP features), with examples including any one of or a function of any one or more of measured N1-P2 latency, N1 latency, P2 latency, N1-P2 range, dynamic CL, dynamic AUC, and any other suitable parameters measured using one or more ECAP features; and the "latency parameter" can be a measured latency parameter (e.g., a time interval directed measured using one or more ECAP features) or calculated as a function (including a weighted function) of one or more measured latency parameters (e.g., each being a time interval directly measured using one or more ECAP features), with examples including any one of or a function of any one or more of measured N1-P2 latency, N1 latency, P2 latency, and any other suitable time intervals measured using one or more ECAP features.

Thus, producing the neural response parameter can include measuring a single neural response parameter or calculating a neural response parameter as a function of multiple measured neural response parameters. Likewise, producing the latency parameter can include measuring a single latency parameter or calculating a latency parameter as a function of multiple measured latency parameters.

In each example of the Examples 1-4, the stimulation current (e.g., pulse amplitude) is used as an example of the dynamically controlled stimulation parameter (i.e., adjusted as a result of executing a closed-loop control algorithm) while one or more other stimulation parameters (e.g., frequency, charge per second, charge per phase, pulse width, burst cycling times, and/or interphase interval) can also be adjusted as a result of executing the closed-loop control algorithm.

In various embodiments, stimulation control circuit 1714 or 1814 can be configured (e.g., programmed) to perform the method (e.g., to execute the algorithm) of each of Examples 1-4. For example, stimulation control circuit 1814 can be configured such that measurement module 1862 produces the neural response parameter, feedback controller 1866 controls the dynamically controlled stimulation parameter, and input analyzer 1864 performs the analysis that uses the neural response parameter produced by measurement module 1862 and produces the outcome using which feedback controller 1866 controls the dynamically controlled stimulation parameter.

Example 1

Figure 20:
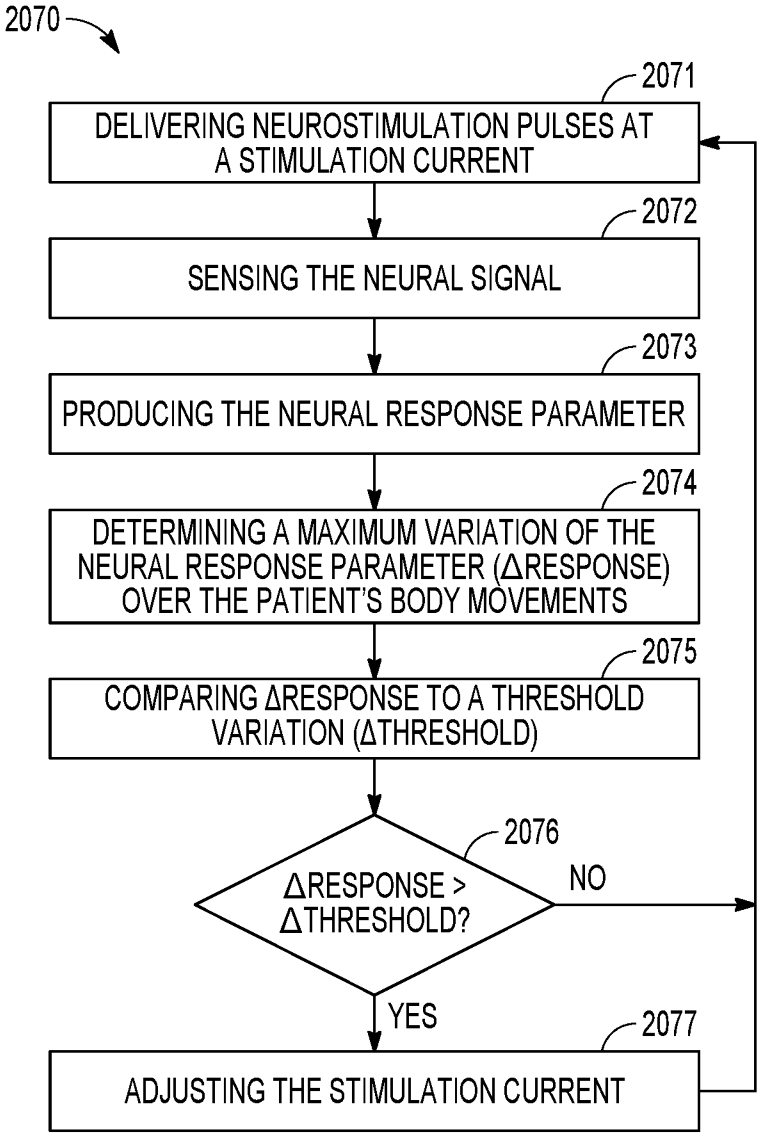
FIG. 20 illustrates an embodiment of a method being a specific example of the method of FIG. 19.

FIG. 20 illustrates an embodiment of a method 2070, which is a stimulation-adjustment algorithm being a specific example of method 1970. At 2071, neurostimulation pulses are delivered at a stimulation current. In various embodiments, threshold parameters are determined by sweeping the stimulation current. The threshold parameters include:

- a neural threshold (NT) being the minimum value of the stimulation current at which the patient starts to feel the paresthesia; and
- a discomfort threshold (DT) being the value of the stimulation current at which the patient starts to feel discomfort.

The stimulation current is set to an amplitude between the NT and the DT for delivering the neurostimulation pulses at 2071. At 2072, the neural signal is sensed. At 2073, the neural response parameter is produced using the neural signal.

At 2074, a maximum variation (slope) of the neural response parameter (ΔResponse) is determined by sensing the neural signal while the patient makes body movements according to a specified series of body postures and/or physical activities. At 2075, ΔResponse is compared to a threshold variation (ΔThreshold). ΔThreshold accounts for factors other than the patients neural activation that affects the sensed neural signal and hence the neural response parameter, e.g., floor noise and natural variability in patient such as respiration, heart rate, ambient activity level, and other baseline fluctuations. Such a threshold allows for determination of whether a detected change in the sensed neural signal is due to anything other than the patient's neural activation change.

If ΔResponse>ΔThreshold (indicating that a neural activation change has occurred) at 2076, the stimulation current is adjusted according to the closed-loop control algorithm at 2077. If ΔResponse≤ΔThreshold (indicating that a neural activation change has not occurred) at 2076, the stimulation current is not to be changed, i.e., the neurostimulation pulses continue to be delivered without adjusting the stimulation current.

In one embodiment, if ΔResponse>ΔThreshold for a specified period of time (indicating that a neural activation change has occurred in a sustaining way) at 2076, the stimulation current is adjusted according to the closed-loop control algorithm at 2077. If ΔResponse≤ΔThreshold or ΔResponse>ΔThreshold only briefly, for less than the specified period of time at 2076, the stimulation current is not to be changed, i.e., the delivery of the neurostimulation pulses continues without adjusting the stimulation current.

Example 2

Figure 21:
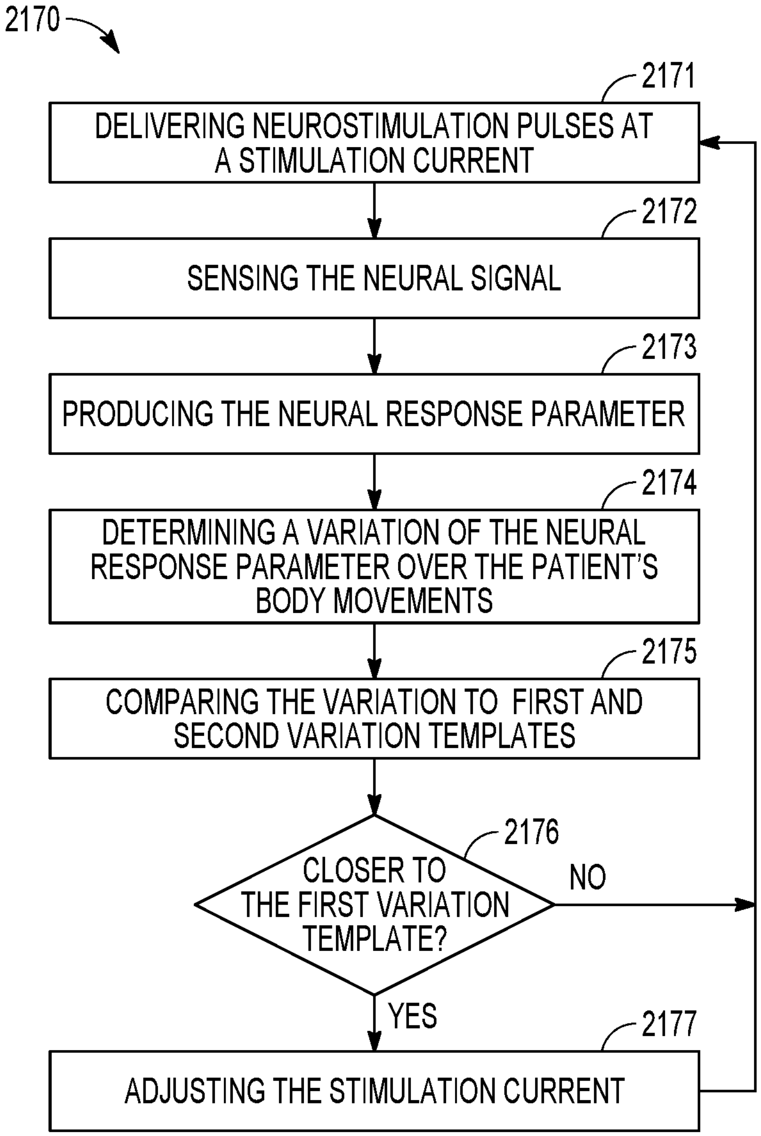
FIG. 21 illustrates an embodiment of a method being another specific example of the method of FIG. 19.

FIG. 21 illustrates an embodiment of a method 2170, which is a stimulation-adjustment algorithm being another specific example of method 1970. At 2171, neurostimulation pulses are delivered at a stimulation current. In various embodiments, threshold parameters including NT and DT are determined by sweeping the stimulation current. The stimulation current is set to an amplitude between the NT and the DT for delivering the neurostimulation pulses at 2171. At 2172, the neural signal is sensed. At 2173, the neural response parameter is produced using the neural signal.

At 2174, a variation (slope) of the neural response parameter is determined by sensing the neural signal while the patient makes body movements according to a specified series of body postures and/or physical activities. At 2175, the variation of the neural response parameter is compared to a template variation including a first template curve of the neural response parameter measured by sweeping the stimulation current while keeping the sensing distance constant and a second template curve of the neural response parameter measured by sweeping the sensing current while keeping the stimulation distance constant. An example of the template variation is shown in FIG. 13, in which the "Sweep Stim Sensing Constant" curve can be used as the first template curve and the "Sweep Sense Stim Constant" curve can be used as the second template curve.

If the variation of the neural response parameter is closer to the first template curve (indicating that a neural activation change has occurred) at 2176, the stimulation current is adjusted according to the closed-loop control algorithm at 2177. If the variation of the neural response parameter is closer to the second template curve (indicating that a neural activation change has not occurred) at 2176, the stimulation current is not to be changed, i.e., the delivery of the neurostimulation pulses continues without adjusting the stimulation current.

In one embodiment, if the variation of the neural response parameter is closer to the first template curve for a specified period of time (indicating that a neural activation change has occurred in a sustaining way) at 2176, the stimulation current is adjusted according to the closed-loop control algorithm at 2177. If the variation of the neural response parameter is closer to the second template curve or the variation of the neural response parameter is closer to the first template curve only briefly, for less than the specified period of time at 2176, the stimulation current is not to be changed, i.e., the delivery of the neurostimulation pulses continues without adjusting the stimulation current.

Example 3

Figure 22:
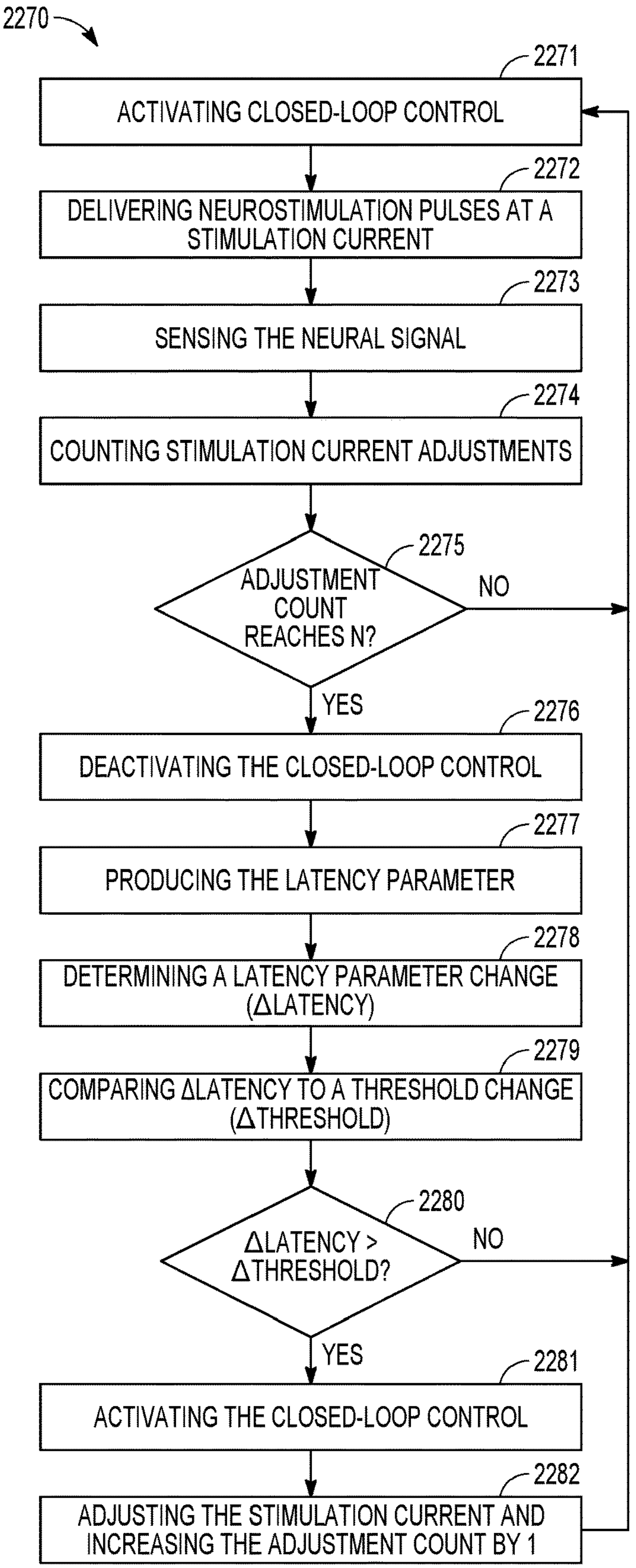
FIG. 22 illustrates an embodiment of a method being yet another specific example of the method of FIG. 19.

FIG. 22 illustrates an embodiment of a method 2270, which is a stimulation-adjustment algorithm being yet another specific example of method 1970. At 2271, closed-loop control for controlling the delivery of the neurostimulation pulses is activated. This can be done, for example, when initiating system 1760. At 2272, neurostimulation pulses are delivered at a stimulation current. In various embodiments, threshold parameters including NT and DT are determined by sweeping the stimulation current. The stimulation current is set to an amplitude between the NT and the DT for delivering the neurostimulation pulses at 2272. At 2273, the neural signal is sensed. At 2274, a number of stimulation current adjustments is counted. This adjustment count is increased by one each time when the stimulation current is adjusted.

If the adjustment count does not reach a specified number N at 2275, the delivery of the neurostimulation pulses continues without adjustment. If the adjustment count reaches N at 2275, closed-loop control is deactivated at 2276. The delivery of the neurostimulation pulses continues without adjusting the stimulation current while the closed-loop control is inactive. At 2277, the latency parameter is produced using the sensed neural signal. At 2278, a latency parameter change (ΔLatency) is determined by comparing the measured value of the latency parameter to a stored previously measured value of the latency parameter (e.g., the value measured at the latest adjustment of the stimulation current). At 2279, ΔLatency is compared to a threshold change (ΔThreshold). ΔThreshold accounts for factors other than the patients neural activation that affects the sensed neural signal and hence the neural response parameter, e.g., floor noise and natural variability in patient such as respiration, heart rate, ambient activity level, and other baseline fluctuations. Such a threshold allows for determination of whether a detected change in the sensed neural signal is due to anything other than the patient's neural activation change.

If ΔLatency≤ΔThreshold (indicating that a neural activation change has not occurred) at 2280, the closed-loop control remains inactive. If ΔLatency>ΔThreshold (indicating that a neural activation change has occurred) at 2280, the closed-loop control is activated at 2281. At 2282, the stimulation current according to the closed-loop control algorithm for N time steps, and the adjustment count is increased by one.

Example 4

Figure 23:
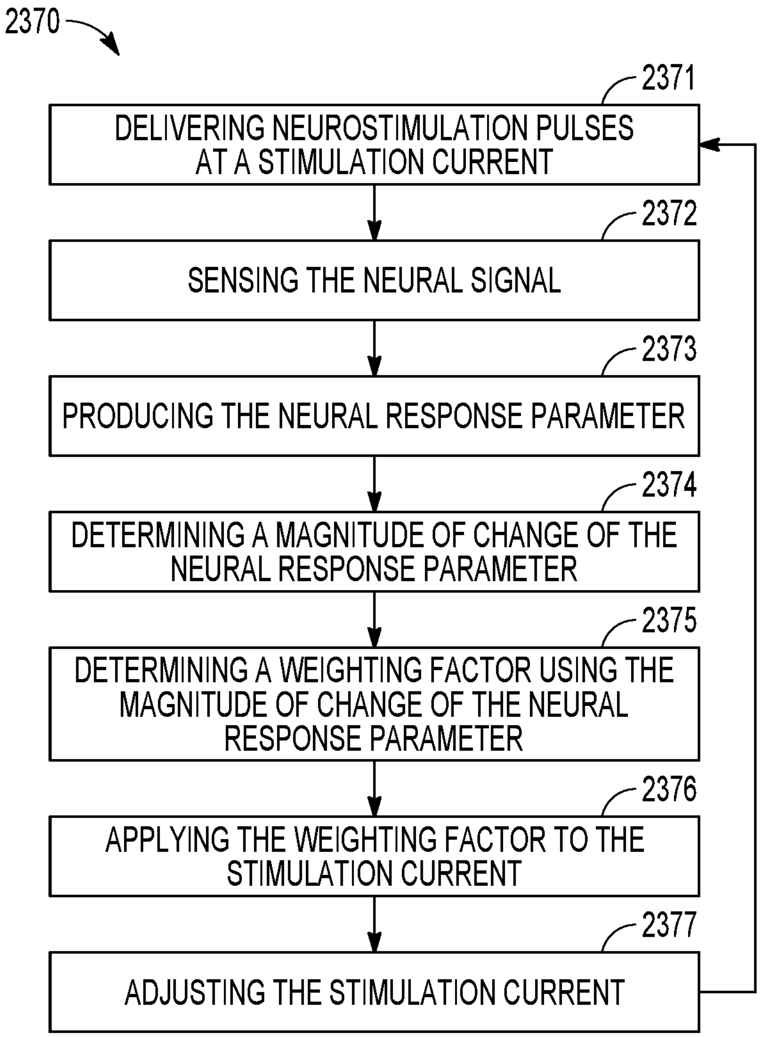
FIG. 23 illustrates an embodiment of a method being still another specific example of the method of FIG. 19.

FIG. 23 illustrates an embodiment of a method 2370, which is a stimulation-adjustment algorithm being still another specific example of method 1970. At 2371, neurostimulation pulses are delivered at a stimulation current. In various embodiments, threshold parameters including NT and DT are determined by sweeping the stimulation current. The stimulation current is set to an amplitude between the NT and the DT for delivering the neurostimulation pulses at 2371. At 2372, the neural signal is sensed. At 2373, the neural response parameter is produced using the neural signal. In various embodiments, the neural response parameter is the latency parameter.

At 2374, a magnitude of change in the neural response parameter is determined. At 2375, a weighting factor is determined using the magnitude of change in the neural response parameter determined at 2374. The weight factor can be proportional the magnitude of change in the neural response parameter. At 2376, the weighting factor is applied to the stimulation current. At 2377, the stimulation current is adjusted using its weighted value produced at 2376. Thus, the amount of adjustment of the stimulation current is proportional to the magnitude of change in the neural response parameter, which represents a degree of likeliness that a neural activate change has occurred. In one embodiment, the weighting factor can be a piecewise linear function of the magnitude of change in the neural response parameter. This avoids adjustment of the stimulation current when, for example, the change in the neural response parameter indicates less than a minimal likeliness that a neural activate change has occurred

Additional Feature Examples

In various embodiments, system 1760 can be configured to perform method 1970 including any one or more of methods 2070, 2170, 2270, and 2370. In addition, system 1760 can be optionally configured and/or used for performing one or more additional methods. The following are non-limiting examples of optional features and methods for expanding functionality and/or enhancing performance of system 1970.

Determining Electrode Shifts

In one embodiment, test (i.e., non-therapeutic by intent) neurostimulation pulses are delivered for determining whether a neural activation change has occurred. The test neurostimulation pulses are defined by test stimulation parameters determined to increase sensitivity for of one or more neural response parameters to the neural activation change. The test stimulation parameters can be empirically determined for increasing the magnitude of the neural response parameter used in the stimulation-adjustment algorithms. One example include a long pulse width (e.g., pulse width>0.5 ms) for detecting changes of the stimulation distance.

In one embodiment, a threshold of the neural response parameter (i.e., the stimulation current needed to cause the neural response parameter to reach a specified value) is determined at multiple pulse widths (e.g., 3 pulse widths), and a strength-duration curve is established using the result. Whether each of the stimulation distance and the sensing distance has changed can then be determined by analyzing changes in the strength-duration curve.

In one embodiment, an artificial neural network is used to determine whether each of the stimulation distance and the sensing distance has changed. This approach can be computationally burdensome but likely yield a superior result.

Identifying Suitable Neural Response Parameter (s)

In one embodiment, machine learning and/or artificial intelligence are used to identify the most suitable neural response parameter for determining whether the neural activation change has occurred for use in the stimulation-adjustment algorithms. The most suitable neural response parameter can be selected from neural response parameters measured and/or calculated from one or more ECAP features (e.g., N1-P2 latency, N1 latency, P2 latency, N1-P2 range, dynamic CL, dynamic AUC, or any combination of these parameters), as discussed above (e.g., with reference to FIG. 12). The selection process can include analyzing effects of changes in the stimulation distances and/or sensing distances on multiple neural response parameters, such as discussed above with references to FIGS. 9-16.

Relating Computational Model to Patient Responses and Multi-Site Calibration As discussed above (e.g., with references to FIGS. 9-16), a computational ECAP model of the spinal cord was used for studying the effects of the patient's body movements on neural responses using simulations. Such a computational model can be related to response of a patient and used to aid custom programming of neurostimulation for the patient, such as in multi-site calibration.

In one embodiment, a model-based curve is received. The model-based curve is a stimulation current-evoked neural response curve generated using one or more computational models. The model-based curve is normalized (e.g., to a model maximum or patient maximum). One or more patient-based curves are received. The one or more patient-based curves are each a stimulation current-evoked neural response curve generated from patient calibration. The model-based curve is compared to the patient-based curve(s). The comparison can include running through scaling factors, multiplying factors, and/or curve fit variables (e.g. if curves are "sigmoidal") until least squares error or other comparison is minimized between model-based curve and the patient-based curves. Using an outcome of the comparison (e.g., based on the best fit), dorsal cerebrospinal fluid (dCSF) layer, spinal position, posture (as a workaround or double-check), medial-lateral (ML) displacement, and/or other pertinent spinal parameters that can affect therapy can be determined (e.g., estimated). The rationale includes that stimulation current-evoked neural response curves can be mapped to specific dCSF thicknesses and/or ML displacements, and determining the best fit of a given curve can be used to assess reliability of estimates of dCSF or ML (i.e. electrode placement). Such curves can be used to expedite establishment of a therapeutic window and/or enable, for example, establishment of a stimulation current-evoked neural response relationship at multiple locations along a lead from a single session (e.g., if vertebral location and dCSF thickness trends are known). Automated adjustment for lead migration can also be possible with such an approach. Stimulation "mini-ramps" can also be configured to be delivered if a sudden perturbation is detected, for example to re-check a dCSF curve to infer patient posture change or lead migration. The stimulation mini-ramps can include, for example, a quick, coarse set of currents ranging incrementally increasing from the previous patient perception threshold to an arbitrary maximum (e.g., a maximum comfortable threshold on the patient's record, an arbitrarily set value, or the like). For example, a stimulation mini-ramp can include ramping a pulse amplitude in a progression from 3.0 mA to 6.0 mA in 0.5 mA steps, with a curve fit or refit occurring over the time interval of the progression. In various embodiments, mini-ramps can include increasing or decreasing one or more stimulation parameters in steps. Sensing can occur during the mini-ramp, and features can be extracted and plotted against the stimulation parameter being ramped to form the curve fit.

In another embodiment, multiple model-based curves are received and compared to the patient-based curve(s). An outcome of the comparison is to determine (e.g., estimate) parameters by identifying a model-based curve that provides the best fit to the patient-based curve from the multiple model-based curves.

In one embodiment, an "auto-spot-check" method is performed to reduce or eliminate the need for recalibrate stimulation and sensing settings for multiple stimulation and sensing electrode locations. Locations and points predicted from the stimulation current-evoked neural response curve (see FIGS. 13-16 for examples of such a curve) are put into a random bin. Several of these locations and points are stochastically selected to "spot-check" the predictions. If the predictions are within a specified accuracy tolerance, the established curves are kept, and automatic stimulation current adjustment with steering or sensing electrode reassignment is enabled. This reduces or eliminates the need for recalibrating for each stimulation and sensing electrode location. In one embodiment, a reference stimulation current-evoked neural response curve is produced from an aggregate patient curve (raw or normalized) to allow for the "auto-spot-check" method to be performed across patients. The reference curve can be used to suggest vertebral or spinal position in the absence of clear imaging. In one embodiment, full calibrations along rostral-caudal (RC) direction is included, though spacing of such calibrations can be adjustable and/or can be held at minimum required to build an RC progression curve.

In various embodiments, relating the computational model to patient responses and multi-site calibration may not help initial programming of the stimulator (e.g., first programming following implantation) in a significantly way but can aid adaptation of neurostimulation therapy for the patient, for example by enabling automatic settings for stimulation field steering and/or automatic adjustment for lead migration. These model-based methods with computational models adapted for the patient can facilitate setting and/or adjustment of sensing and/or stimulation parameters for the patient when needed for new or changed electrode locations relative to the spinal cord.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient, the system comprising:

a stimulation output circuit configured to deliver the neurostimulation;

a sensing circuit configured to sense a neural signal indicative of neural responses, the neural responses each being a response to the delivery of the neurostimulation; and a stimulation control circuit coupled to the stimulation output circuit and the sensing circuit, the stimulation control circuit configured to control the delivery of the neurostimulation using a plurality of stimulation parameters and including:

a measurement module configured to detect morphological features of the neural responses and to produce a neural response parameter using the detected morphological features;

an input analyzer configured to detect a change in the sensed neural signal and to analyze the produced neural response parameter for attributing the detected change to a neural activation change in the patient or a body movement of the patient to indicate a likeliness of occurrence of the neural activation change; and a feedback controller configured to control a dynamically controlled stimulation parameter of the plurality of stimulation parameters using the sensed neural signal according to the indicated likeliness of occurrence of the neural activation change.

2. The system of claim 1, wherein the stimulation output circuit is configured to deliver neurostimulation pulses, the sensing circuit is configured to sense a neural signal indicative of evoked compound action potentials (ECAPs) each evoked by a pulse of the neurostimulation pulses, and the measurement module is configured to detect ECAP features each being a morphological feature of the ECAPs and to produce the neural response parameter using the detected ECAP features.

3. The system of claim 2, wherein the measurement module is configured to detect at least one of a first negative peak (N1) or a second positive peak (P2) of the ECAP features and to measure at least one of:

an N1-P2 Latency being a time interval between N1 and P2;

an N1 latency being a time interval between delivery of a pulse of the neurostimulation pulses and N1;

a P2 latency a time interval between delivery of a pulse of the neurostimulation pulses and P;

an N1-P2 Range being a difference between amplitudes of N1 and P2;

a dynamic curve length (CL) being a curve length measured from the sensed neural signal between N1 and P2; or a dynamic area under the curve (AUC) being an area under the sensed neural signal measured between N1 and P2.

4. The system of claim 2, wherein the input analyzer is configured to determine whether the detected change indicates a neural activation change has occurred, and the feedback controller is configured to adjust the dynamically controlled stimulation parameter in response to a determination that the neural activation change has occurred and to keep the dynamically controlled stimulation parameter unchanged in response to a determination that the neural activation change has not occurred.

5. The system of claim 4, wherein the input analyzer is configured to:

determine a maximum variation of the neural response parameter for a segment of the neural signal sensed during body movements of the patient; and compare the maximum variation of the neural response parameter to a threshold variation, and the feedback controller is configured to:

adjust the dynamically controlled stimulation parameter in response to the maximum variation of the neural response parameter exceeding the threshold variation; and keep the dynamically controlled stimulation parameter unchanged in response to the maximum variation of the neural response parameter not exceeding the threshold variation.

6. The system of claim 4, wherein the input analyzer is configured to:

determine a variation of the neural response parameter for a segment of the neural signal sensed during body movements of the patient; and compare the variation of the neural response parameter to each of a first variation template and a second variation template, and the feedback controller is configured to:

adjust the dynamically controlled stimulation parameter in response to the variation of the neural response parameter being closer to the first variation template than to the second variation template; and keep the dynamically controlled stimulation parameter unchanged in response to the variation of the neural response parameter being closer to the second variation template than to the first variation template.

7. The system of claim 4, wherein the neural response parameter is a latency parameter being a time interval associated with at least one of the detected ECAP features, the input analyzer is configured to:

deactivate the feedback controller in response to an adjustment count reaching a specified value N;

determine a change of the latency parameter by a current value of the latency parameter to a previous value of the latency parameter;

compare the change of the latency parameter change to a threshold change;

activate the feedback controller in response to the change of the latency parameter change exceeding the threshold change; and keep the feedback controller inactivated in response to the change of the latency parameter change not exceeding the threshold change, and the feedback controller is configured to:

adjust the dynamically controlled stimulation parameter when being activated; and increase the adjustment count by 1 in response to each adjustment.

8. The system of claim 2, wherein the input analyzer is configured to determine a weighting factor as a function of the neural response parameter, and the feedback controller is configured to apply the weighting factor to the dynamically controlled stimulation parameter and to adjust the weighted dynamically controlled stimulation parameter.

9. The system of claim 8, wherein the neural response parameter is a latency parameter being a time interval associated with at least one of the detected ECAP features.

10. A non-transitory computer-readable storage medium including instructions, which when executed by a system, cause the system to perform a method for delivering neurostimulation to a patient, the method comprising:

delivering the neurostimulation;

sensing a neural signal indicative of neural responses, the neural responses each being a response to the delivery of the neurostimulation; and controlling the delivery of the neurostimulation using a plurality of stimulation parameters, including:

detecting morphological features of the neural responses;

producing a neural response parameter using the detected morphological features;

detecting a change in the sensed neural signal;

analyzing the produced neural response parameter for attributing the detected change to a neural activation change in the patient or a body movement of the patient to indicate a likeliness of occurrence of the neural activation change; and controlling a dynamically controlled stimulation parameter of the plurality of stimulation parameters using the sensed neural signal according to the indicated likeliness of occurrence of the neural activation change.

11. A method for delivering neurostimulation to a patient, the method comprising:

delivering the neurostimulation from a stimulation output circuit;

sensing a neural signal indicative of neural responses using a sensing circuit, the neural responses each being a response to the delivery of the neurostimulation; and controlling the delivery of the neurostimulation using a processor using a plurality of stimulation parameters, including:

detecting morphological features of the neural responses;

producing a neural response parameter using the detected morphological features;

detecting a change in the sensed neural signal;

analyzing the produced neural response parameter for attributing the detected change to a neural activation change in the patient or a body movement of the patient to indicate a likeliness of occurrence of the neural activation change; and controlling a dynamically controlled stimulation parameter of the plurality of stimulation parameters using the sensed neural signal according to the indicated likeliness of occurrence of the neural activation change.

12. The method of claim 11, further comprising identifying a suitable type of parameter to be the neural response parameter using at least one of machine learning or artificial intelligence.

13. The method of claim 11, wherein delivering the neurostimulation comprises delivering neurostimulation pulses, sensing the neural signal comprises sensing a neural signal indicative of evoked compound action potentials (ECAPs) each evoked by a pulse of the neurostimulation pulses, detecting the morphological features of the neural responses comprises detecting ECAP features each being a morphological feature of the ECAPs, and producing the neural response parameter comprises producing the neural response parameter using the detected ECAP features.

14. The method of claim 13, wherein producing the neural response parameter comprises measuring two or more parameters using the detected ECAP features and calculating the neural response parameter as a function of the measured two or more parameters.

15. The method of claim 13, wherein detecting the ECAP features comprises detecting at least one of a first negative peak (N1) or a second positive peak (P2), and producing the neural response parameter comprises measuring at least one of:

an N1-P2 Latency being a time interval between N1 and P2;

an N1 latency being a time interval between delivery of a pulse of the neurostimulation pulses and N1;

a P2 latency a time interval between delivery of a pulse of the neurostimulation pulses and P;

an N1-P2 Range being a difference between amplitudes of N1 and P2;

a dynamic curve length (CL) being a curve length measured from the sensed neural signal between N1 and P2; or a dynamic area under the curve (AUC) being an area under the sensed neural signal measured between N1 and P2.

16. The method of claim 13, further comprising determining whether the detected change indicates a neural activation change has occurred using the processor, and wherein controlling the dynamically controlled stimulation parameter comprises adjusting the dynamically controlled stimulation parameter in response to a determination that the neural activation change has occurred and keeping the dynamically controlled stimulation parameter unchanged in response to a determination that the neural activation change has not occurred.

17. The method of claim 16, wherein determining whether the detected change indicates a neural activation change has occurred comprises:

determining a maximum variation of the neural response parameter for a segment of the neural signal sensed during body movements of the patient; and comparing the maximum variation of the neural response parameter to a threshold variation, and controlling the dynamically controlled stimulation parameter comprises:

adjusting the dynamically controlled stimulation parameter in response to the maximum variation of the neural response parameter exceeding the threshold variation; and keeping the dynamically controlled stimulation parameter unchanged in response to the maximum variation of the neural response parameter not exceeding the threshold variation.

18. The method of claim 16, determining whether the detected change indicates a neural activation change has occurred comprises:

determining a variation of the neural response parameter for a segment of the neural signal sensed during body movements of the patient; and comparing the variation of the neural response parameter to each of a first variation template and a second variation template, and controlling the dynamically controlled stimulation parameter comprises:

adjusting the dynamically controlled stimulation parameter in response to the variation of the neural response parameter being closer to the first variation template than to the second variation template; and keeping the dynamically controlled stimulation parameter unchanged in response to the variation of the neural response parameter being closer to the second variation template than to the first variation template.

19. The method of claim 16, wherein the neural response parameter is a latency parameter being a time interval associated with at least one of the detected ECAP features, determining whether the detected change indicates a neural activation change has occurred comprises:

deactivating a closed-loop control in response to an adjustment count reaching a specified value N;

determining a change of the latency parameter by a current value of the latency parameter to a previous value of the latency parameter;

comparing the change of the latency parameter change to a threshold change;

activating the closed-loop control in response to the change of the latency parameter change exceeding the threshold change; and keep the closed-loop control inactivated in response to the change of the latency parameter change not exceeding the threshold change, and controlling the dynamically controlled stimulation parameter comprises:

adjusting the dynamically controlled stimulation parameter according to the closed-loop control when being activated; and increasing the adjustment count by 1 in response to each adjustment.

20. The method of claim 11, wherein determining whether the detected change indicates a neural activation change has occurred comprises determining a weighting factor as a function of the neural response parameter, and controlling the dynamically controlled stimulation parameter comprises:

applying the weighting factor to the dynamically controlled stimulation parameter; and adjusting the weighted dynamically controlled stimulation parameter.

* * * * *